United States Patent
Ghosh

(10) Patent No.: US 11,752,347 B2
(45) Date of Patent: Sep. 12, 2023

(54) CARDIAC CONDUCTION SYSTEM PACING

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/360,648

(22) Filed: Jun. 28, 2021

(65) Prior Publication Data

US 2022/0032062 A1     Feb. 3, 2022

Related U.S. Application Data

(60) Provisional application No. 63/066,521, filed on Aug. 17, 2020, provisional application No. 63/059,466, filed on Jul. 31, 2020.

(51) Int. Cl.
| | |
|---|---|
| *A61N 1/368* | (2006.01) |
| *A61N 1/37* | (2006.01) |
| *A61N 1/375* | (2006.01) |
| *A61N 1/39* | (2006.01) |

(52) U.S. Cl.
CPC ......... *A61N 1/3682* (2013.01); *A61N 1/3688* (2013.01); *A61N 1/3706* (2013.01); *A61N 1/37512* (2017.08); *A61N 1/39622* (2017.08)

(58) Field of Classification Search
CPC .... A61N 1/0215; A61N 1/0587; A61N 1/365; A61N 1/3682; A61N 1/3688; A61N 1/3706; A61N 1/3711; A61N 1/37217; A61N 1/37235; A61N 1/37512; A61N 1/3756; A61N 2001/0585; A61B 5/346; A61B 5/365

See application file for complete search history.

(56) References Cited

U.S. PATENT DOCUMENTS

| | | |
|---|---|---|
| 4,374,382 A | 2/1983 | Markowitz |
| 4,624,265 A | 11/1986 | Grassi |
| 5,117,824 A | 6/1992 | Keimel et al. |
| (Continued) | | |

FOREIGN PATENT DOCUMENTS

| | | |
|---|---|---|
| EP | 1234597 A2 | 8/2002 |
| WO | WO 2006/069215 A2 | 6/2006 |
| (Continued) | | |

OTHER PUBLICATIONS

U.S. Appl. No. 61/819,946, filed May 6, 2013.
(Continued)

*Primary Examiner* — Brian T Gedeon
(74) *Attorney, Agent, or Firm* — Mueting Raasch Group

(57) ABSTRACT

The present disclosure relates generally to pacing of the cardiac conduction system of a patient, and more particularly, to providing adaptive cardiac conducting system pacing therapy and to determining selective or non-selective capture of the cardiac conduction system by cardiac conduction system pacing therapy. The adaptive cardiac conduction system pacing therapy may adjust AV delay and VV delay based on various signals and metrics and may switch between cardiac conduction system pacing therapy exclusively and cardiac conduction system pacing therapy in combination with traditional left ventricular pacing therapy.

16 Claims, 14 Drawing Sheets

(56) References Cited

U.S. PATENT DOCUMENTS

| | | | |
|---|---|---|---|
| 5,174,286 A | 12/1992 | Chirife | |
| 5,545,186 A | 8/1996 | Olsen et al. | |
| 5,728,140 A | 3/1998 | Salo et al. | |
| 5,755,736 A | 5/1998 | Gillberg et al. | |
| 5,800,467 A | 9/1998 | Park et al. | |
| 5,964,795 A | 10/1999 | McVenes et al. | |
| 6,556,866 B2 | 4/2003 | Dal Molin et al. | |
| 6,609,027 B2 | 8/2003 | Kroll et al. | |
| 6,711,443 B2 | 3/2004 | Osypka | |
| 6,718,206 B2 | 4/2004 | Casvant | |
| 6,738,674 B2 | 5/2004 | Osypka | |
| 6,768,923 B2 | 7/2004 | Ding et al. | |
| 6,804,555 B2 | 10/2004 | Warkentin | |
| 6,988,007 B1 | 1/2006 | Morgan et al. | |
| 7,177,704 B2 | 2/2007 | Laske et al. | |
| 7,191,015 B2 | 3/2007 | Lamson et al. | |
| 7,386,351 B2 | 6/2008 | Hine et al. | |
| 7,647,124 B2 | 1/2010 | Williams | |
| 7,729,782 B2 | 6/2010 | William et al. | |
| 7,738,954 B1 | 6/2010 | Kroll et al. | |
| 7,792,580 B2 | 9/2010 | Borowitz et al. | |
| 7,801,624 B1 | 9/2010 | Flannery et al. | |
| 7,815,577 B2 | 10/2010 | Krishnan | |
| 8,013,133 B2 | 9/2011 | Sharma et al. | |
| 8,078,287 B2 | 12/2011 | Liu et al. | |
| 8,112,160 B2 | 2/2012 | Foster | |
| 8,321,014 B2 | 11/2012 | Maskara et al. | |
| 8,406,899 B2 | 3/2013 | Reddy et al. | |
| 8,560,068 B2 | 10/2013 | Forslund | |
| 8,565,880 B2 | 10/2013 | Dong et al. | |
| 8,588,907 B2 | 11/2013 | Arcot-krishnamurthy et al. | |
| 8,606,369 B2 | 12/2013 | Williams et al. | |
| 8,688,234 B2 | 4/2014 | Ortega et al. | |
| 8,761,880 B2 | 6/2014 | Maskara et al. | |
| 8,834,384 B2 | 9/2014 | Krishnan | |
| 8,874,237 B2 | 10/2014 | Schilling et al. | |
| 8,942,805 B2 | 1/2015 | Shuros et al. | |
| 8,954,147 B2 | 2/2015 | Arcot-krishnamurthy et al. | |
| 9,101,281 B2 | 8/2015 | Reinert et al. | |
| 9,162,066 B2 | 10/2015 | Hedberg et al. | |
| 9,168,382 B2 | 10/2015 | Shuros et al. | |
| 9,550,058 B2 | 1/2017 | Foster | |
| 9,789,319 B2 | 10/2017 | Sambelashvil | |
| 10,850,107 B2 * | 12/2020 | Li | A61N 1/056 |
| 10,850,108 B2 | 12/2020 | Li et al. | |
| 2003/0023295 A1 | 1/2003 | Osypka et al. | |
| 2003/0023296 A1 | 1/2003 | Osypka et al. | |
| 2003/0199938 A1 | 10/2003 | Smits et al. | |
| 2003/0199956 A1 | 10/2003 | Struble et al. | |
| 2004/0054388 A1 | 3/2004 | Osypka | |
| 2004/0153127 A1 | 8/2004 | Gordon et al. | |
| 2006/0095107 A1 | 5/2006 | Osypka | |
| 2006/0206153 A1 | 9/2006 | Libbus et al. | |
| 2007/0016261 A1 | 1/2007 | Dong et al. | |
| 2007/0078490 A1 | 4/2007 | Cowan et al. | |
| 2008/0082136 A1 | 4/2008 | Gaudiani | |
| 2008/0177344 A1 | 7/2008 | Maskara et al. | |
| 2008/0288008 A1 | 11/2008 | Lee | |
| 2009/0177344 A1 | 7/2009 | James et al. | |
| 2010/0069983 A1 | 3/2010 | Peacock, III et al. | |
| 2011/0264158 A1 | 10/2011 | Dong et al. | |
| 2011/0319956 A1 | 12/2011 | Zhu et al. | |
| 2012/0101539 A1 | 4/2012 | Zhu et al. | |
| 2012/0101542 A1 | 4/2012 | Arcot-Krishnamurthy et al. | |
| 2012/0310101 A1 | 12/2012 | Patantgay et al. | |
| 2013/0079861 A1 | 3/2013 | Reinert et al. | |
| 2013/0090701 A1 | 4/2013 | Liu et al. | |
| 2013/0158621 A1 | 6/2013 | Ding et al. | |
| 2014/0018892 A1 | 1/2014 | Dahlberg | |
| 2014/0046389 A1 | 2/2014 | Anderson et al. | |
| 2014/0107723 A1 | 4/2014 | Hou et al. | |
| 2014/0107724 A1 | 4/2014 | Shuros et al. | |
| 2014/0172035 A1 | 6/2014 | Shuros et al. | |
| 2014/0277239 A1 | 9/2014 | Maskara et al. | |
| 2015/0045811 A1 | 2/2015 | Schilling | |
| 2015/0217110 A1 | 8/2015 | Ollivier | |
| 2016/0339248 A1 | 11/2016 | Schrock et al. | |
| 2017/0304624 A1 | 10/2017 | Friedman et al. | |
| 2017/0340887 A1 | 11/2017 | Engels et al. | |
| 2018/0256904 A1 | 9/2018 | Li et al. | |
| 2019/0022378 A1 | 1/2019 | Prillinger et al. | |
| 2019/0111264 A1 | 4/2019 | Zhou | |
| 2019/0111265 A1 | 4/2019 | Zhou | |
| 2019/0111270 A1 | 4/2019 | Zhou | |
| 2019/0126040 A1 | 5/2019 | Shuros et al. | |
| 2019/0126049 A1 | 5/2019 | Casavant et al. | |
| 2019/0126050 A1 | 5/2019 | Shuros et al. | |
| 2019/0134404 A1 | 5/2019 | Sheldon et al. | |
| 2019/0134405 A1 | 5/2019 | Sheldon et al. | |
| 2019/0192092 A1 | 6/2019 | Hahn et al. | |
| 2019/0192860 A1 | 6/2019 | Ghosh et al. | |
| 2019/0201698 A1 | 7/2019 | Herrmann et al. | |
| 2019/0217097 A1 | 7/2019 | Thakur et al. | |
| 2019/0275329 A1 | 9/2019 | Brisben et al. | |
| 2019/0290918 A1 | 9/2019 | Ghosh | |
| 2020/0016395 A1 | 1/2020 | Makharinsky | |
| 2020/0179692 A1 * | 6/2020 | Ternes | A61N 1/3624 |
| 2020/0261725 A1 | 8/2020 | Yang et al. | |
| 2020/0261734 A1 | 8/2020 | Yang et al. | |
| 2020/0353265 A1 * | 11/2020 | Ghosh | A61N 1/365 |
| 2021/0085986 A1 | 3/2021 | Li et al. | |

FOREIGN PATENT DOCUMENTS

| | | | |
|---|---|---|---|
| WO | WO 2010/071849 A2 | 6/2010 | |
| WO | WO 2014/055692 A2 | 4/2014 | |
| WO | WO 2017/192892 A2 | 11/2017 | |

OTHER PUBLICATIONS

U.S. Appl. No. 17/360,648, filed Jun. 28, 2021.

U.S. Appl. No. 17/361,721, filed Jun. 29, 2021.

International Search Report and Written Opinion for PCT/US2018/056242, dated Feb. 11, 2019, 16 pages.

International Preliminary Report on Patentability for PCT/US2018/056242, dated Apr. 30, 2020, 9 pages.

International Search Report and Written Opinion for PCT/US2018/056257, dated Jan. 3, 2019, 16 pages.

International Preliminary Report on Patentability for PCT/US2018/056257, dated Apr. 30, 2020, 9 pages.

International Search Report and Written Opinion for PCT/US2018/056292, dated Jan. 30, 2019, 16 pages.

International Preliminary Report on Patentability for PCT/US2018/056292, dated Apr. 30, 2020, 9 pages.

International Search Report and Written Opinion for PCT/US2018/056295, dated Dec. 19, 2018, 18 pages.

International Preliminary Report on Patentability for PCT/US2018/056295, dated Apr. 30, 2020, 9 pages.

International Search Report and Written Opinion for PCT Application No. PCT/US2020/016468 dated May 7, 2020, 10 pages.

International Search Report and Written Opinion for PCT Application No. PCT/US2020/016369 dated May 26, 2020, 10 pages.

International Search Report and Written Opinion for PCT Application No. PCT/US2021/042940 dated Nov. 3, 2021, 11 pages.

Abdelrahman et al., "Clinical Outcomes of His Bundle Pacing Compared to Right Ventricular Pacing," *J Am Coll Cardiol.*, May 22, 2018; 71(20):2319-2330.

Ahmed et al., "Right Ventricular Apical Pacing-induced Left Ventricular Dyssynchrony is Associated with a Subsequent Decline in Ejection Fraction," *Heart Rhythm*, Apr. 2014; 11(4):602-608.

Ajijola et al., "Permanent His-bundle pacing for cardiac resynchronization therapy: Initial feasibility study in lieu of left ventricular lead," *Heart Rhythm*, Sep. 2017; 14(9):1353-1361.

Al-Hesayen et al., "Adverse effects of atrioventricular synchronous right ventricular pacing on left ventricular sympathetic activity, efficiency, and hemodynamic status," *Am J Physiol Heart Circ Physiol.*, 2006; 291(5):H2377-H2379.

Anderson et al., "Wilhelm His Junior and his bundle," *J Electrocardiol.*, 2016; 49:637-643.

(56) References Cited

OTHER PUBLICATIONS

Babu et al., "Three-dimensional echocardiography with left ventricular strain analyses helps earlier prediction of right ventricular pacing-induced cardiomyopathy," *J Saudi Heart Assoc.*, Apr. 2018;30(2):102-107.

Barba-Pichardo et al., "Permanent His-Bundle Pacing in patients with Infra-Hisian Atrioventricular Block," *Revista Espanola de Cardiologia*, Jun. 2006; 59(6):553-558.

Cantú et al., "Validation of Criteria for Selective His Bundle and Para-Hisian Permanent Pacing," *Pacing & Clinical Electrophysiology*, Dec. 2006; 29(12):1326-1333.

Catanzari et al., "Permanent His-Bundle Pacing Maintains Long-Term Ventricular Synchrony and Left Ventricular Performance, Unlike Conventional Right Ventricular Apical Pacing," *EP Europace*, Apr. 2013; 15(4):546-553.

Chang et al., "Tricuspid Valve Dysfunction Following Pacemaker or Cardioverter-Defibrillator Implantation," *J Am Coll Cardiol.*, May 9, 2017; 69(18): 2331-2341.

Cho et al., Cerclage parahisian septal pacing through the septal perforator branch of the great cardiac vein: Bedside-to-bench development of a novel technique and lead, *Heart Rhythm Society*, Dec. 2019;16(12):1834-1840.

Chon et al., "TCT-18: Novel Concept of Catheter-Based Treatment for Tricuspid Regurgitation(Cerclage-TR block)," Pusan National University Yangsan Hospital, Yangsan, South Korea NHLBI, NIH, USA* Sep. 21, 2018.

Choy et al., "Right ventricular pacing impairs endothelial function in man," *Europace*, Jun. 2011; 13(6):853-858.

Dandamudi et al., "My Approach to Choosing Ventricular Pacing Sites in Patients With Severe Heart Failure," *J Cardio Electrophysiol.*, Jul. 2011; 22(7):813-817.

Dandamudi et al., "How to perform permanent His bundle pacing in routine clinical practice," *Heart Rhythm Society*, Jun. 2016; 13(6):1362-1366.

Dandamudi et al., "The Complexity of the His Bundle: Understanding Its Anatomy and Physiology through the Lens of the Past and the Present," Sep. 2016, DOI: 10.1111/pace.12925.

De Sisti et al., "Adverse Effects of Long-Term Right Ventricular Apical Pacing and Identification of Patients at Risk of Atrial Fibrillation and Heart Failure," PACE, Aug. 2012; 35(8):1035-1043.

Deshmukh et al., "Permanent, Direct His-Bundle Pacing: A Novel Approach to Cardiac Pacing in Patients With Normal Hus-Purkinje Activation," *Circulation*, Feb. 29, 2000, 101(8):869-877.

Deshmukh et al., "Direct His-Bundle Pacing: Present and Future," *PACE*, Jun. 2004; 27 [6 Pt.2]:862-70.

Deshmukh et al., "Direct His-Bundle Triple Site Pacing: A Novel Alternative to Bi-Ventricular Pacing," Heart Rhythm 2009, Presentation Abstract, May 14, 2009.

Deshmukh et al. "Comparison of Direct His Bundle and Biventricular Pacing," Heart Rhythm 2009, Poster Session V, May 15, 2009.

Deshmukh et al., "His bundle pacing: Initial experience and lessons learned," *J Electrocardiol.*, 2016; 49:658-663.

Dreger et al., "Pacing-induced cardiomyopathy in patients with right ventricular stimulation for >15 years," *EP Europace*, Feb. 2012; 14(2):238-242.

El-Sherif et al., "Normalization of Bundle Branch Block Patterns by Distal His Bundle Pacing. Clinical and Experimental Evidence of Longitudinal Dissociation in the Pathologic His Bundle," *Circulation*, Mar. 1978; 57:473-83.

Friedman et al., "Intermittent Capture of the Left Bundle With Permanent His Bundle Pacing: Mechanistic Insights and Implications for an Emerging Field," Aug. 1, 2016. doi: 10.1111/jce.13057.

Fröhlig et al., "His-bundle Stimulation and Alternative RV Stimulation Sites," Mar. 2008; 19(1):30-40, German.

Garrote et al., "His Bundle Pacing: Great in Theory, But Difficult in Practice," Revista Española de Cardiología, 2006; 59(6):534-6.

Gierula et al., "Pacing-associated left ventricular dysfunction? Think reprogramming first!" *Heart*, May 2014; 100(10):765-769.

Gierula et al., "Patients with long-term permanent pacemakers have a high prevalence of left ventricular dysfunction," *J Cardiovasc Med*, Nov. 2015: 16(11):743-750.

Gillis et al., "Atrial Fibrillation After DDDR Pacemaker Implantation," *J Cardiovasc Electrophysiol.*, Jun. 2002;13(6):542-547.

Gula et al., "Feasibility of His Bundle Pacing as an Alternative Pacing Site: Measurement of His Refractoriness," *J Interv Card Electrophysiol.*, 2005; 12: 69-73.

Hayashi et al., "Impact of simple electrocardiographic markers as predictors for deterioration of left ventricular function in patients with frequent right ventricular apical pacing," *Heart Vessels*, Sep. 26, 2017; 33(3):299-308.

"His-Bundle Pacing Papers" http://www.his.pacing.org/the-list-his-bundle-pacing-papers/, 15 pages.

Hoyt et al., "Reversal of Left Ventricular Dysfunction with Biventricular or His-bundle Pacing Upgrade Late after A-V Nodal Ablation/block," Heart Rhythm 2008 29th Scientific Sessions.

Hoyt et al., "Hemodynamic Evaluation of Direct His-Bundle and Parahisian Pacing," Heart Rhythm 2009, Poster Session V, May 15, 2009.

Huang et al., "Benefits of Permanent His Bundle Pacing Combined With Atrioventricular Node Ablation in Atrial Fibrillation Patients With Heart Failure With Both Preserved and Reduced Left Ventricular Ejection Fraction," *J Am Heart Assoc.*, Apr. 1, 2017; 6(4). pii: e005309.

Huang et al., "Feasibility of His Bundle Pacing in Correct Left Bundle Branch Block in Heart Failure Patients," Journal of the American College of Cardiology, vol. 70, No. 16, Suppl C, 2017, GW28-e1237, 1 page.

Karpawich et al., "Septal His-Purkinje Ventricular Pacing in Canines: A New Endocardial Electrode Approach," *Pacing Clinical Electrophysiology*, 1992: 15:2011-5.

Karpawich et al., "Altered Cardiac Histology Following Apical Right Ventricular Pacing in Patients with Congenital Atrioventricular Block," *Pacing Clin Electrophysiol.*, Sep. 1999; 22(9):1372-7.

Khoo et al., "Right Ventricular Pacing as Backup to His Bundle Pacing to Minimize Battery Drain," Heart Rhythm Society, Scientific Sessions, 2013.

Kiehl et al., "Incidence and predictors of right ventricular pacing-induced cardiomyopathy in patients with complete atrioventricular block and preserved left ventricular systolic function," *Heart Rhythm*, Dec. 2016; 13(12):2272-2278.

Kim et al., "Trans-coronary sinus intraseptal para-Hisian pacing: Cerclage pacing," *Heart Rhythm*, Apr. 2016, 13(4):992-6.

Kim, "Mitral Loop Cerclage a catheter-based treatment of functional mitral regurgitation (CSTV)," JCR 2019, EuroPCR 2018.

Kronborg et al., "Left Ventricular Performance during para-His Pacing in Patients with High-degree Atrioventricular Block: an acute study," *Europace*, Jun. 2014; 14(6):841-6. Epub Dec. 14, 2011.

Kronborg et al., "His or para-His Pacing Preserves Left Ventricular Function in AV Block: a Double-blind, Randomized, Crossover Study," *Europace*, Aug. 2014; 16(8): 1189-96.

Kronborg et al., "Left ventricular regional remodeling and lead position during cardiac resynchronization therapy," *Heart Rhythm*, Apr. 17, 2018; 15(10):542-1549.

Kronborg et al., "His Bundle Pacing: Techniques and Outcomes," *Curr Cardiol Rep.*, Jul. 2016;18(8):76.

Laske et al., "Excitation of the Intrinsic Conduction System Through His and Interventricular Septal Pacing," *PACE*, Apr. 2006; 29(4):397-405.

Lederman et al., "Mitral Cerclage Annuloplasty," Cadiovascular Intervention Program at NHLBI, Update 2017.

Lindsay, "Deleterious Effects of Right Ventricular Pacing," *The New England Journal of Medicine*, Nov. 15, 2009; 361:2183-2185.

Lustgarten et al., "Direct His Bundle Pacing vs. BiVentricular Pacing in CRT Patients—A Cross-over Design Comparison," *Heart Rhythm*, 2013.

Lustgarten et al., "His-Bundle vs Biventricular Pacing in Resynchronization Therapy," *Heart Rhythm*, Jul. 2015; 12(7):1548-1557.

Lustgarten et al., "Step-wise Approach to Permanent His Bundle Pacing," *The Journal of Innovations in Cardiac Rhythm Management*, 2016; 7:2313-2321.

(56) References Cited

OTHER PUBLICATIONS

Mabo et al., "A Technique for Stable His-bundle Recording and Pacing: Electrophysiological and Hemodynamic Correlates," *Pacing Clinical Electrophysiology*,1995; 18:1894-901.

Mazza et al., "Incidence and Predictors of Heart Failure Hospitalization and Death in Permanent Pacemaker Patients: a Single-Center Experience over Medium-term Follow-up," Europace (2013) 15. 1267-1272.

Naperkowski et al., "Direct Implantation of Permanent His Bundle Pacing Lead in Patients with Complete Heart Block Without a Mapping Catheter or a Back-up Right Ventricular Lead: Feasibility and One year Follow-up," *Heart Rhythm*, Scientific Sessions, 2013.

Narula, "Longitudinal Dissociation in the His Bundle," *Circulation*, Dec. 1977; 56(6):996-1006.

Niazi et al., "Comparison of Lead Placement Strategies for Permanent His Bundle Pacing," Supplement, May 2011; 8(5).

Occhetta et al., "Prevention of Ventricular Desynchronization by Permanent Para-Hisian Pacing after Atrioventricular Node Ablation in Chronic Atrial Fibrillation," *Journal of the American College of Cardiology*, May 16, 2006; 47(10):1938-45.

Occhetta et al., "Future Easy and Physiological Cardiac Pacing," *Journal of Cardiology*, Jan. 26, 2011; 31(1):32-39.

Padeletti et al., "Rate Stabilization by Right Ventricular Apex or His Bundle Pacing in Patients With Atrial Fibrillation," *Europace*, 2005; 7:454-459.

Pastore et al., "Hisian area and Right Ventricular Apical Pacing Differently Affected Left Atrial Function: an Intra-patient Evaluation," *Europace*; 2013.

Pastore et al., "The Risk of Atrial Fibrillation during Right Ventricular Pacing," *Europace*, Mar. 2016; 18(3):353-8.

Scheinman et al., "Long-term His-Bundle Pacing and Cardiac Function," *Circulation* Feb. 29, 2000; 101:836-837.

Scherlag et al., "Functional aspects of His bundle physiology and pathophysiology: Clinical implications," *J Electrocardiol.*, Jan.-Feb. 2017; 50(1)151-155.

Sharma et al., "Permanent His-bundle Pacing is Feasible, Safe, and Superior to Right Ventricular Pacing in Routine Clinical Practice," *Heart Rhythm*, Feb. 2015; 12(2):305-312.

Sharma, "His Bundle Pacing or Biventricular Pacing for Cardiac Resynchronization Therapy in Heart Failure: Discovering New Methods for an Old Problem," *J Atr Fibrillation*, Dec. 31, 2016.

Sharma et al., "Permanent His Bundle Pacing for Cardiac Resynchronization Therapy in Patients With Heart Failure and Right Bundle Branch Block," *Circ Arrhythm Electrophysiol.*, Sep. 2018;11(9):e006613.

Sharma et al., "Safety and Feasibility of Permanent His Bundle Pacing Without a Guiding Mapping Catheter or a Back-Up Right Ventricular Lead in Routine Clinical Practice", Heart Rhythm, vol. 10, No. 5, May 2013, 1 page.

Su et al., "Pacing and sensing optimization of permanent His-bundle pacing in cardiac resynchronization therapy/implantable cardioverter defibrillators patients: value of integrated bipolar configuration," *EP Europace*, 18(9):1399-1405.

Sweeney et al., "Adverse Effect of Ventricular Pacing on Heart Failure and Atrial Fibrillation Among Patients With Normal Baseline QRS Duration in a Clinical Trial of Pacemaker Therapy for Sinus Node Dysfunction," *Circulation*, Jun. 17, 2003; 107(23):2932-2937.

Teng et al., "Physiological mechanisms of QRS narrowing in bundle branch block patients undergoing permanent His bundle pacing," *J Electrocardiol.*, 2016; 49(5):644-648.

Teng et al., "Usefulness of His Bundle Pacing to Achieve Electrical Resynchronization in Patients With Complete Left Bundle Branch Block and the Relation Between Native QRS Axis, Duration, and Normalization," *American Journal of Cardiology*, May 28, 2016; 118(4):527-534.

Thambo et al., "Detrimental ventricular remodeling in patients with congenital complete heart block and chronic right ventricular apical pacing," *Circulation*, Dec. 21, 2004; 110(25):3766-72.

Vijayaraman et al., "Permanent His Bundle Pacing in Patients with Advanced Heart Block: Single Center Experience in Unselected Patients Without Mapping Catheter or Back-Up RV Pacing Lead," Heart Rhythm Society, Scientific Sessions, 2014.

Vijayaraman et al., "Anatomical approach to permanent His bundle pacing: Optimizing His bundle capture," *J Electrocardiol.*, 2016; 49: 649-657.

Vijayaraman et al., "How to Perform Permanent His Bundle Pacing: Tips and Tricks," *Pacing Clin Electrophysiol.*, Dec. 2016; 39(12):1298-1304.

Vijayaraman et al., "The Continued Search for Physiological Pacing Where Are We Now?" *Journal of the American College of Cardiology*, Jun. 27, 2017; 69(25):3099-3114.

Vijayaraman et al., "His Bundle Injury Current during Implantation of Permanent His Bundle Pacing Lead Predicts Excellent Pacing Outcomes," Heart Rhythm Society, Scientific Sessions, 2014.

Vijayaraman et al., "Acute His-Bundle Injury Current during Permanent His-Bundle Pacing Predicts Excellent Pacing Outcomes," Pacing Clinical Electrophysiology, Jan. 14, 2015. doi: 10.1111/pace.12571.

Vijayaraman et al., "Electrophysiologic Insights Into Site of Atrioventricular Block: Lessons From Permanent His Bundle Pacing," *JACC: Clinical Electrophysiology*, Dec. 2015; 1(6):571-581.

Vijayaraman et al., "Permanent His bundle pacing: Electrophysiological and echocardiographic observations from long-term follow-up," *PACE*, Jul. 2017; 40:883-891.

Vijayaraman et al., "Permanent His Bundle Pacing (HBP): Recommendations From A Multi-Center HBP Collaborative Working Group for Standardization of Definitions, Implant Measurements and Follow-Up," Oct. 2017; DOI: http://dx.doi.org/10.1016/j.hrthm.

Vijayaraman et al., "His Bundle Pacing," *Journal of the American College of Cardiology*, Aug. 2018; 72(8).

Wilson et al., "Strategically targeting calcium: Altering activation sequence to reverse remodel the failing ventricle," *Heart Rhythm*, Oct. 2018;15(10):1550-1551.

Worsnick et al., "Direct His Bundle Pacing in a Patient with Complete Heart Block Requiring Implantable Defibrillator," *The Journal of Innovation in Cardiac Rhythm Management*, Aug. 2013; 492.

Yamauchi et al., "Permanent His-Bundle Pacing After Atrioventricular Node Ablation in a Patient With Chronic Atrial Fibrillation and Mitral Regurgitation," *Circ J*, 2005;69:510-514.

Zanon et al., "A Feasible Approach for Direct His-Bundle Pacing Using a new Steerable Catheter to Facilitate Precise Lead Placement," *JCE*, Jan. 2006; 17:29-33.

Zanon et al., "Direct His Bundle Pacing Preserves Coronary Perfusion Compared With Right Ventricular Apical Pacing: a Prospective, Cross-over Mid-term Stud," *Europace*; May 2008;10(5):580-7.

Zanon et al., "Safety and Performance of a System Specifically Designed for Selective Site Pacing," *Pacing and Clinical Electrophysiology*, Mar. 2011; 34(3):339-347.

Zanon et al., "Direct His bundle and Parahisian Cardiac Pacing," *A.N.E.*, Apr. 2012; 17(2):70-8.

Znojkiewicz et al., "Direct His-bundle Pacing in Patients Following AV Node Ablation," Heart Rhythm, May 2011; 8(5):Supplement.

International Search Report and Written Opinion from PCT Application No. PCT/US2021/042943 dated Jan. 11, 2022, 15 pages.

International Search Report and Written Opinion from PCT Application No. PCT/US2021/042948 dated Oct. 27, 2021, 10 pages.

* cited by examiner

CARDIAC CONDUCTION SYSTEM PACING

This application claims the benefit of U.S. Provisional Patent Application Ser. No. 63/059,466, filed on Jul. 31, 2020, entitled "Cardiac Conduction System Pacing" and U.S. Provisional Patent Application Ser. No. 63/066,521, filed on Aug. 17, 2020, entitled "Cardiac Conduction System Pacing," each of which are incorporated by reference herein in their entireties.

The present disclosure relates generally to pacing of the cardiac conduction system of a patient, and more particularly, to providing adaptive cardiac conducting system pacing therapy and to determining selective or non-selective capture of the cardiac conduction system by cardiac conduction system pacing therapy.

Implantable medical devices (IMDs), such as cardiac pacemakers or implantable cardioverter defibrillators, deliver therapeutic stimulation to patients' hearts thereby improving the lives of millions of patients living with heart conditions. Conventional pacing techniques involve pacing one or more of the four chambers of patient's heart 12—left atrium (LA) 33, right atrium (RA) 26, left ventricle (LV) 32 and right ventricle (RV) 28, all of which are shown in FIG. 1. One common conventional therapeutic pacing technique that treats a slow heart rate, referred to as Bradycardia, involves delivering an electrical pulse to a patient's right ventricular tissue. In response to the electrical pulse, both the right and left ventricles contract. However, the heart beat process may be significantly delayed because the pulse travels from the right ventricle through the left ventricle. The electrical pulse passes through the muscle cells that are referred to as myocytes. Myocyte-to-myocyte conduction may be very slow. Delayed electrical pulses can cause the left ventricle to be unable to maintain synchrony with the right ventricle.

Over time, the left ventricle can become significantly inefficient at pumping blood to the body. In some patients, heart failure can develop such that the heart is too weak to pump blood to the body. Heart failure may be a devastating diagnosis since, for example, fifty percent of the heart failure patients have a life expectancy of five years. To avoid the potential development of heart failure, some physicians have considered alternative pacing methods that involve the cardiac conduction system. The cardiac conduction system, like a "super highway," may be described as quickly conducting electrical pulses whereas pacing cardiac muscle tissue may slowly conduct electrical pulses, like "traveling on a dirt road."

The cardiac conduction system includes sinoatrial node (SA node) 1, atrial internodal tracts 2, 4, 5 (i.e., anterior internodal 2, middle internodal 4, and posterior internodal 5), atrioventricular node (AV node) 3, His bundle 13 (also known as atrioventricular bundle or bundle of His), and right and left bundle branches 8a, 8b. FIG. 1 also shows the arch of aorta 6 and Bachman's bundle 7. The SA node, located at the junction of the superior vena cava and right atrium, is considered to be the natural pacemaker of the heart since it continuously and repeatedly emits electrical impulses. The electrical impulse spreads through the muscles of right atrium 26 to left atrium 33 to cause synchronous contraction of the atria. Electrical impulses are also carried through atrial internodal tracts to atrioventricular (AV) node 3—the sole connection between the atria and the ventricles. Conduction through the AV nodal tissue takes longer than through the atrial tissue, resulting in a delay between atrial contraction and the start of ventricular contraction. The AV delay, which is the delay between atrial contraction and ventricular contractor, allows the atria to empty blood into the ventricles. Then, the valves between the atria and ventricles close before causing ventricular contraction via branches of the bundle of His. His bundle 13 is located in the membranous atrioventricular septum near the annulus of the tricuspid valve. His bundle 13 splits into right and left bundle branches 8a, 8b and are formed of specialized fibers called "Purkinje fibers" 9. Purkinje fibers 9 may be described as rapidly conducting an action potential down the ventricular septum (VS), spreading the depolarization wavefront quickly through the remaining ventricular myocardium, and producing a coordinated contraction of the ventricular muscle mass.

While cardiac conduction system pacing therapy is increasingly used as an alternative to traditional pacing techniques, cardiac conduction system pacing therapy has not been widely adopted for a variety of reasons. For example, cardiac conduction system pacing electrodes should be positioned within precise target locations (e.g., within about 1 millimeter) of portions or regions of the cardiac conduction system, such as the His bundle, which may be difficult. Additionally, adjustment of cardiac conduction system pacing therapy during delivery of therapy may be challenging. Further, determination of whether the cardiac conduction system pacing therapy is selective (i.e., only pacing the cardiac conduction system) or non-selective (i.e., pacing both the cardiac conduction system and the myocardial tissue) may also be challenging. It is desirable to develop new cardiac conduction system pacing therapy systems, devices, and methods and systems that overcome some of the disadvantages associated with previously-performed cardiac conduction system pacing therapies.

SUMMARY

This disclosure generally relates to pacing the cardiac conduction system such as, for example, the His-Purkinje system, including His bundle, left bundle branches, and right bundle branches. In particular, illustrative devices and methods are described herein to provide adaptive cardiac conduction system pacing therapy that may selectively provide pacing therapy in conjunction with traditional left ventricular pacing therapy. Such adaptive cardiac conduction system pacing therapy may be able to determine and adjust an AV delay and a VV delay (between the cardiac conduction system pacing therapy and traditional left ventricular pacing therapy) based on near-field or far-field signals so as to be able to provide effective cardiac therapy to a patient. Additionally, such adaptive cardiac conduction system pacing therapy may be able switch between cardiac conduction system pacing therapy alone and cardiac conduction system pacing therapy in combination with traditional left ventricular pacing therapy so as to be able to provide effective cardiac therapy to a patient.

The illustrative devices and methods may be described as utilizing a triple-chamber device solution for cardiac resynchronization therapy-indicated patients that may include a standard right atrial lead, a 3830 or 3830 D lead for His or left bundle branch (LBB) area pacing, and an left ventricular lead. The illustrative devices and methods may use one or more processes for adaptive left ventricular pacing based on efficacy of left ventricular activation from His/LBB area pacing. Such processes may "'adapt'" between His or LBB area only pacing and His or LBB area in conjunction with left ventricular pacing based on an electrocardiogram based efficacy metric for preactivation of the left ventricle with conduction system pacing.

One illustrative implantable medical device may include a plurality of implantable electrodes to sense and pace a patient's heart. The plurality of electrodes may include a left ventricular electrode positionable proximate the patient's left ventricle and a cardiac conduction system electrode positionable proximate a portion of the patient's cardiac conduction system. The deice may further include a computing apparatus comprising processing circuitry. The computing apparatus may be operably coupled to the plurality of implantable electrodes and configured to initiate delivery of cardiac conduction system pacing therapy to the patient's cardiac conduction system using the cardiac conduction system electrode and monitor local electrical activity of the patient using the left ventricular electrode during the delivery of cardiac conduction system pacing therapy using the cardiac conduction system electrode. The computing apparatus may be further configured to switch to delivery of both cardiac conduction system pacing therapy to the patient's cardiac conduction system using the cardiac conduction system electrode and left ventricular pacing therapy to the patient's left ventricle using the left ventricular electrode in response to the monitored local electrical activity.

One illustrative method may include delivering cardiac conduction system pacing therapy to a patient's cardiac conduction system using a cardiac conduction system electrode implanted proximate a portion of the patient's cardiac conduction system and monitoring local electrical activity of the patient using a left ventricular electrode implanted proximate the patient's left ventricle during the delivery of cardiac conduction system pacing therapy using the cardiac conduction system electrode. The illustrative method may further include switching to delivery of both cardiac conduction system pacing therapy to the patient's cardiac conduction system using the cardiac conduction system electrode and left ventricular pacing therapy to the patient's left ventricle using the left ventricular electrode in response to the monitored local electrical activity.

One illustrative implantable medical device may include a plurality of implantable electrodes to sense and pace a patient's heart. The plurality of electrodes may include a left ventricular electrode positionable proximate the patient's left ventricle and a cardiac conduction system electrode positionable proximate a portion of the patient's cardiac conduction system. The deice may further include a computing apparatus comprising processing circuitry. The computing apparatus may be operably coupled to the plurality of implantable electrodes and configured to determine a paced AV delay for use in delivery of cardiac conduction system pacing therapy using the cardiac conduction system electrode. The paced AV delay is a time period between an atrial event and delivery of cardiac conduction system pacing therapy. The computing apparatus may be further configured to determine a paced VV delay for use in delivery of cardiac conduction system pacing therapy using the cardiac conduction system electrode and delivery of left ventricular pacing therapy using the left ventricular electrode. The paced VV delay is a time period between the delivery of the left ventricular pacing therapy and the delivery of the cardiac conduction system pacing therapy. The computing apparatus may be further configured to deliver either cardiac conduction system pacing therapy using the paced AV delay or cardiac conduction system pacing therapy and left ventricular pacing therapy using the paced AV delay and the paced VV delay.

One illustrative method may include determining a paced AV delay for use in delivery of cardiac conduction system pacing therapy using a cardiac conduction system electrode implanted proximate a portion of the patient's cardiac conduction system. The paced AV delay is a time period between an atrial event and delivery of cardiac conduction system pacing therapy. The illustrative method may further include determining a paced VV delay for use in delivery of cardiac conduction system pacing therapy using the cardiac conduction system electrode and delivery of left ventricular pacing therapy using a left ventricular electrode implanted proximate the patient's left ventricle. The paced VV delay is a time period between the delivery of the left ventricular pacing therapy and the delivery of the cardiac conduction system pacing therapy. The illustrative method may further include delivering either cardiac conduction system pacing therapy using the paced AV delay or cardiac conduction system pacing therapy and left ventricular pacing therapy using the paced AV delay and the paced VV delay.

Left bundle branch (LBB) area pacing may be important for treating both bradycardia and heart failure, left bundle branch block (HF-LBBB) patients for correcting left bundle branch block. It may be described that LBB is an optimal area for physiologic pacing. However, distinction of selective versus non-selective capture of the LBB may be important for titrating optimal pacing at the LBB. Selective capture includes capture of the left bundle branch without local myocardial capture and is closer to physiologic or normal activation of left bundle branch compared to non-selective pacing. Non-selective pacing also involves cell-to-cell stimulation of the septal area and may provide a slower path of whole-heart activation than selective. The illustrate devices and methods may utilize a near-field electrogram based device diagnostic for distinguishing between selective and non-selective capture, which may be important for long-term monitoring of efficacy of left bundle pacing. With the goal being selective capture, if non-selective capture is detected, one or more pacing parameters (e.g., pacing outputs, vectors, etc.) may be adjusted to achieve selective capture.

Illustrative devices and methods are described herein to provide cardiac conduction system pacing therapy and to determine whether such cardiac conduction system pacing therapy has selectively or non-selectively captured the cardiac conduction system. Cardiac conduction system pacing therapy having selective capture of the cardiac conduction system may be defined as pacing therapy that delivers pacing therapy only to the cardiac conduction system and that does not delver pacing therapy directly to myocardial or muscular cardiac tissue. In other words, selective cardiac conduction system pacing therapy paces the cardiac conduction system alone. Cardiac conduction system pacing therapy having non-selective capture of the cardiac conduction system may be defined as pacing therapy that delivers pacing therapy to the cardiac conduction system and directly to the myocardial or muscular cardiac tissue. In other words, non-selective cardiac conduction system pacing therapy paces both the cardiac conduction system and myocardial or muscular cardiac tissue. The illustrative devices and methods, using a near-field signal, may be able to determine whether the delivered cardiac conduction system pacing therapy is selective or non-selective, which may be helpful in delivery effective cardiac therapy to a patient.

One illustrative implantable medical device may include a plurality of implantable electrodes to sense and pace a patient's heart and a computing apparatus comprising processing circuitry. The computing apparatus may be operably coupled to the plurality of implantable electrodes and configured to initiate a delivery of pacing therapy to the patient's heart, monitor a near-field signal over a sensing time period proximate the left bundle branch using the plurality of implantable electrodes following the delivery of pacing therapy, generate a derivative signal based on the near-field signal, and determine whether the pacing therapy has selective or non-selective capture of the cardiac conduction system based on the derivative signal.

One illustrative method may include delivering pacing therapy to the patient's heart using one or more of a plurality of implantable electrodes, monitoring a near-field signal over a sensing time period proximate the left bundle branch using the plurality of implantable electrodes following the delivery of pacing therapy, generating a derivative signal based on the near-field signal, and determining whether the pacing therapy has selective or The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION

Figure 1:
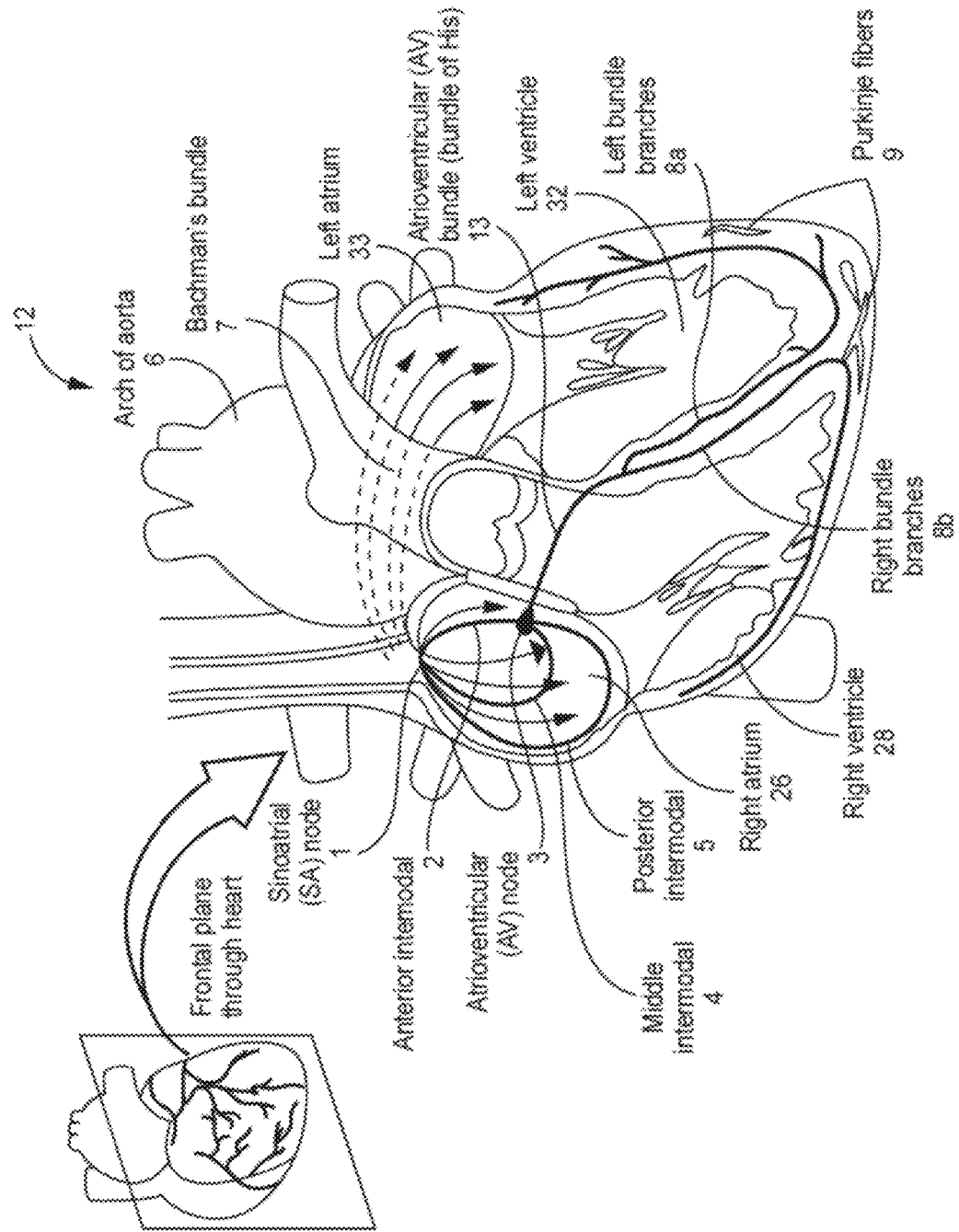
FIG. 1 is a schematic diagram of a heart of patient (prior art).

In the following detailed description of illustrative embodiments, reference is made to the accompanying figures of the drawing which form a part hereof, and in which are shown, by way of illustration, specific embodiments which may be practiced. It is to be understood that other embodiments may be utilized, and structural changes may be made without departing from (e.g., still falling within) the scope of the disclosure presented hereby.

Illustrative devices and methods shall be described with reference to FIGS. 1-12. It will be apparent to one skilled in the art that elements or processes from one embodiment may be used in combination with elements or processes of the other embodiments, and that the possible embodiments of such devices and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Figure 2A:
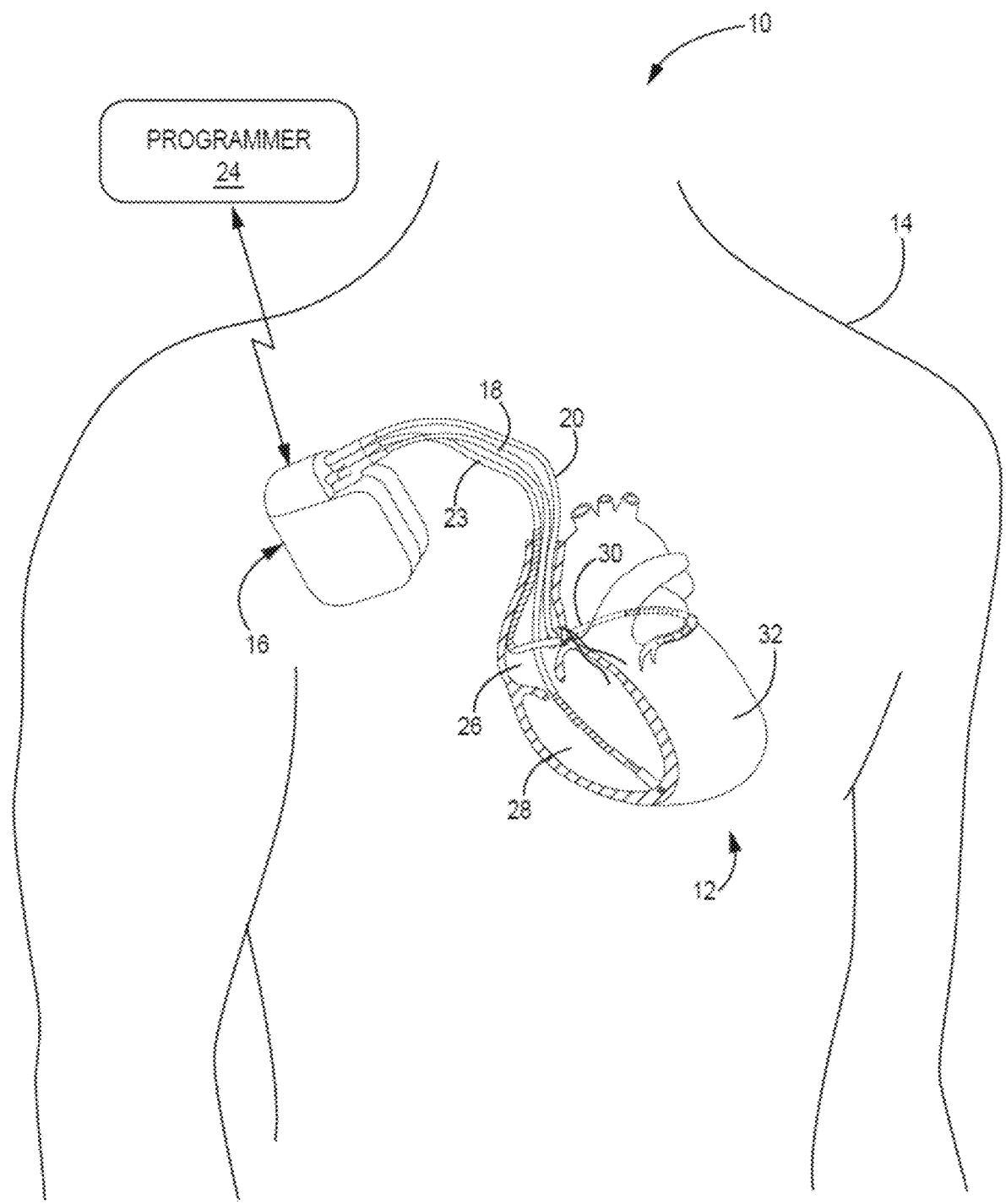
FIG. 2A is a conceptual diagram illustrating an example therapy system (e.g., triple-chamber implantable medical device) that is configured to provide therapy to a heart of patient through a His-bundle or bundle-branch pacing lead and lead placed either in the right ventricle or the right atrium using an implantable medical device (IMD).
Figure 2B:
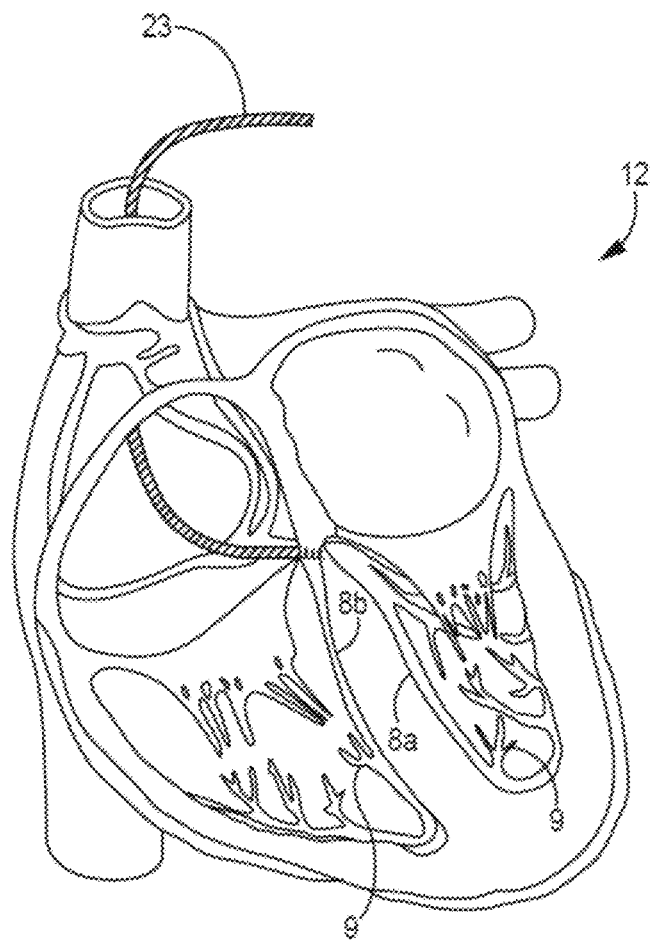
FIG. 2B is a schematic diagram illustrating an example His-bundle or bundle-branch pacing lead positioned in bundle of the His in a cross-sectional view of the heart.

FIGS. 2A-2B are conceptual diagrams illustrating one example therapy system 10 that may be used to provide therapy to heart 12 of patient 14. Patient 14 ordinarily, but not necessarily, will be a human. Therapy system 10 includes IMD 16, which is coupled to leads 18, 20, 23 and programmer 24. IMD 16 may be, for example, an implantable pacemaker, cardioverter, and/or defibrillator that provides electrical signals to heart 12 via electrodes coupled to one or more of leads 18, 20, 23. Further non-limiting examples of IMD 16 include: a pacemaker with a medical lead, an implantable cardioverter-defibrillator (ICD), an intracardiac device, a leadless pacing device (LPD), a subcutaneous ICD (S-ICD), and a subcutaneous medical device (e.g., nerve stimulator, inserted monitoring device, etc.).

Leads 18, 20, 23 extend into heart 12 of patient 14 to sense electrical activity of heart 12 and/or deliver electrical stimulation to heart 12. In the example shown in FIG. 2A, right ventricular (RV) lead 18 extends through one or more veins (not shown), the superior vena cava (not shown), and right atrium (RA) 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Cardiac conduction system pacing therapy lead 23 (e.g., His-bundle or bundle-branch pacing lead) extends through one or more veins and the vena cava, and into the right atrium 26 of heart 12 to pace the cardiac conduction system (e.g., triangle of Koch, septal wall, left bundle branch, right bundle branch, the His bundle, etc.). In some embodiments, the cardiac conduction system pacing therapy lead 23 may be positioned within about 1 millimeter of the triangle of Koch, septal wall, His bundle, or one or both bundle branches.

As used herein, cardiac conduction system pacing therapy refers to any pacing therapy configured to deliver pacing therapy (e.g., pacing pulses) to the cardiac conduction system including, e.g., the His bundle, left bundle branch, right bundle branch, etc. As used herein, the term "activation" refers to a sensed or paced event. For example, an atrial activation may refer to an atrial sense or event (As) or an atrial pace or artifact of atrial pacing (Ap). Similarly, a ventricular activation may refer to a ventricular sense or event (Vs) or a ventricular pace or artifact of ventricular pacing (Vp), which may be described as ventricular stimulation pulses. In some embodiments, activation interval can be detected from As or Ap to Vs or Vp, as well as Vp to Vs. In particular, activation intervals may include a pacing (Ap or Vp) to ventricular interval (LV or RV sense) or an atrial-sensing (As) to ventricular-sensing interval (LV or RV sense).

One example of a cardiac conduction system pacing therapy lead 23 (e.g., a His lead) can be the S ELECTSURE™ 3830. A description of the SELECTSURE™ 3830 is found in the Medtronic model SELECTSURE™ 3830 manual (2013), incorporated herein by reference in its entirety. The SELECTSURE™ 3830 includes two or more conductors with or without lumens.

An elongated conductor of the lead may extend through a hermetic feedthrough assembly, and within an insulative tubular member of the lead, and may electrically couple an electrical pulse generator (contained within housing) to the helical tip electrode, or cardiac conduction system electrode, of the cardiac conduction system pacing therapy lead 23. The conductor may be formed by one or more electrically conductive wires, for example, MP35N alloy known to those skilled in the art, in a coiled or cabled configuration, and the insulative tubular member may be any suitable medical grade polymer, for example, polyurethane, silicone rubber, or a blend thereof. According to an illustrative embodiment, the flexible lead body extends a pre-specified length (e.g., about 10 centimeters (cm) to about 20 cm, or about 15 to 20 cm) from a proximal end of housing to the other end. The lead body is less than about 7 French (FR) but typically in the range of about 3 to 4 FR in size. In one or more embodiments, about 2 to about 3 FR size lead body is employed.

Cardiac conduction system pacing therapy can be performed by other leads. Another illustrative lead, including two or more pacing electrodes, can be used to deliver multisite pacing pulses to the bundle of His or one or both bundle branches. Multisite pacing can be delivered simultaneously or sequentially, as described and shown by U.S. Patent Publication No. 2016/0339248, filed on Apr. 21, 2016, entitled EFFICIENT DELIVERY OF MULTI-SITE PACING, the disclosure of which is incorporated by reference in its entirety.

Since the electrodes in multi-site or multi-point stimulation may be in close proximity to each other, it may be important to detect and verify effective capture of individual electrodes during delivery of such therapy. Delivering multisite pacing pulses may include delivering pacing pulses to a first tissue site and a second tissue site through first and second pacing electrodes, respectively, all of which may occur within the same cardiac cycle.

In particular, a lead configured to perform multi-site pacing, which is different than LV coronary sinus lead 20, can be placed in the ventricular septum with the first (distal) electrode on the left side of the ventricular septum for left bundle branch pacing and with the second electrode (proximal) on the right side of the septum for pacing the right bundle branch. An interelectrode distance may be defined as the distance between the first and second electrodes, or the distance that the electrodes are apart. In some embodiments, the interelectrode distance is at least about 3, 4, 5, 6, 7, or 8 millimeters (mm). In some embodiments, the interelectrode distance is at most about 15, 14, 13, 12, 11, or 10 mm. For example, the interelectrode distance may be in a range from about 6 to 12 mm apart. Once the pacing is delivered, both the left bundle branch and the right bundle branch may be stimulated such that both ventricles are naturally or near-naturally synchronized. In contrast, in traditional CRT, the ventricles may be described as not naturally synchronized.

A single lead, including two (or more) pacing electrodes (e.g., cathodes) may deliver cathode pacing outputs at two separate locations (e.g., left and right bundle branches), so both bundle branches can be excited at the same time.

His bundle pacing, though a leading candidate for physiological pacing, may be hard to implant, may have a relatively high pacing threshold, and may have an unstable long-term pacing threshold in patients with conduction disease. Bundle branch pacing may bypass the pathological region and may have a low and stable pacing threshold. In some embodiments, only one bundle branch may be paced by using pacing leads. One aspect of this disclosure provides pacing of both bundle branches at the same time (e.g., dual bundle branch pacing), which may mimic intrinsic activation propagation via the His bundle-Purkinje conduction system, e.g., paced activation propagates via both bundle branches to both ventricles for synchronized contraction. Traditional His bundle pacing, on the other hand, typically paces the His bundle proximal to the bundle branches. In some embodiments, IMD 16 may include one, two, or more electrodes located in one or more bundle branches configured for bundle branch pacing. In some embodiments, IMD 16 may be an intracardiac pacemaker or leadless pacing device (LPD).

As used herein, "leadless" refers to a device being free of a lead extending out of patient's heart 12. In other words, a leadless device may have a lead that does not extend from outside of the patient's heart to inside of the patient's heart. Some leadless devices may be introduced through a vein, but once implanted, the devices are free of, or may not include, any transvenous lead and may be configured to provide cardiac therapy without using any transvenous lead. In one or more embodiments, an LPD for bundle pacing does not use a lead to operably connect to an electrode disposed proximate to the septum when a housing of the device is positioned in the atrium. A leadless electrode may be leadlessly coupled to the housing of the medical device without using a lead between the electrode and the housing.

IMD 16 may sense electrical signals attendant to the depolarization and repolarization of heart 12 via electrodes (not shown in FIGS. 2A-B) coupled to at least one of leads 18, 20, 23. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of leads 18, 20, 23. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In some examples, programmer 24 (FIG. 1) may be a handheld computing device or a computer workstation or a mobile phone. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. Through the graphical user interface on programmer 24, a user may select one or more optimized parameters.

Additionally, various pacing settings may be adjusted, or configured, based on various sensed signals. For example, various near-field and far-field signals may be sensed by one or more electrodes of the IMD 16 and/or other devices operatively coupled thereto. For example, Vp to QRS end or offset within a near-field or far-field signal may be used to adjust or configure the AV delay of cardiac conduction system pacing therapy. Further, for example, QRS within a near-field or far-field signal may be used to adjust or configure the VV delay between cardiac conduction system pacing therapy and traditional left ventricular pacing therapy. Still further, left bundle branch electrocardiogram following a post-blanking time period after ventricular pacing may be analyzed determine whether cardiac conduction system pacing therapy is selective or non-selective. Thus, QRS complexes may be detected using near field and/or far-field electrical signals. For example, the far-field electrical signals may be sensed in a far-field electrogram (EGM) monitored by IMD 16 and a corresponding lead or a separate device, such as a subcutaneously implanted device. QRS duration is the time from which the Q wave is detected until the S wave ends.

As used herein, the term "far-field" electrical signal refers to the result of measuring cardiac activity using a sensor, or electrode, positioned outside of an area of interest. For example, an ECG signal measured from an electrode positioned outside of the patient's heart is one example of a far-field electrical signal of the patient's heart. As another example, a far-field electrical signal representing electrical activity of a chamber of the patient's heart may be measured from a sensor, or electrode, positioned in an adjacent chamber.

As used herein, the term "near-field" electrical signal refers to the result of measuring cardiac activity using a sensor, or electrode, positioned near an area of interest. For example, an EGM signal measured from an electrode positioned on the left side of the patient's ventricular septum is one example of a near-field electrical signal of the patient's LV.

R-wave timing is the time in which QRS is detected. Typically, R-wave timing includes using the maximal first derivative of an R-wave upstroke (or the time of the maximal R-wave value). R-wave timing is also used in the device marker channel to indicate the time of the R-wave or the time of ventricular activation.

Pacing-RV sensing or pacing-LV sensing (e.g., pacing-to-RV sensing or pacing-to-LV sensing) is the time interval from the pacing (or pacing artifact) to the time of RV or LV sensing. For example, if pacing-RV sensing is much longer than pacing-LV sensing, this may indicate that the LV activation is occurring much earlier than RV activation (so pacing-RV sensing is longer), then RV pacing may be delivered in synchronization with bundle pacing, so RV and LV activation can occur approximately at the same time.

A user, such as a physician, technician, or other clinician, may interact with programmer 24 to communicate with IMD 16. For example, the user may interact with programmer 24 to retrieve physiological or diagnostic information from IMD 16. One illustrative IMD 16 is described in the Medtronic AMPLIA MRI™ CRT-D SURESCAN™ DTMB2D1 manual, which is incorporated by reference in its entirety. A user may also interact with programmer 24 to program IMD 16, e.g., select values for operational parameters of the IMD.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 3A:
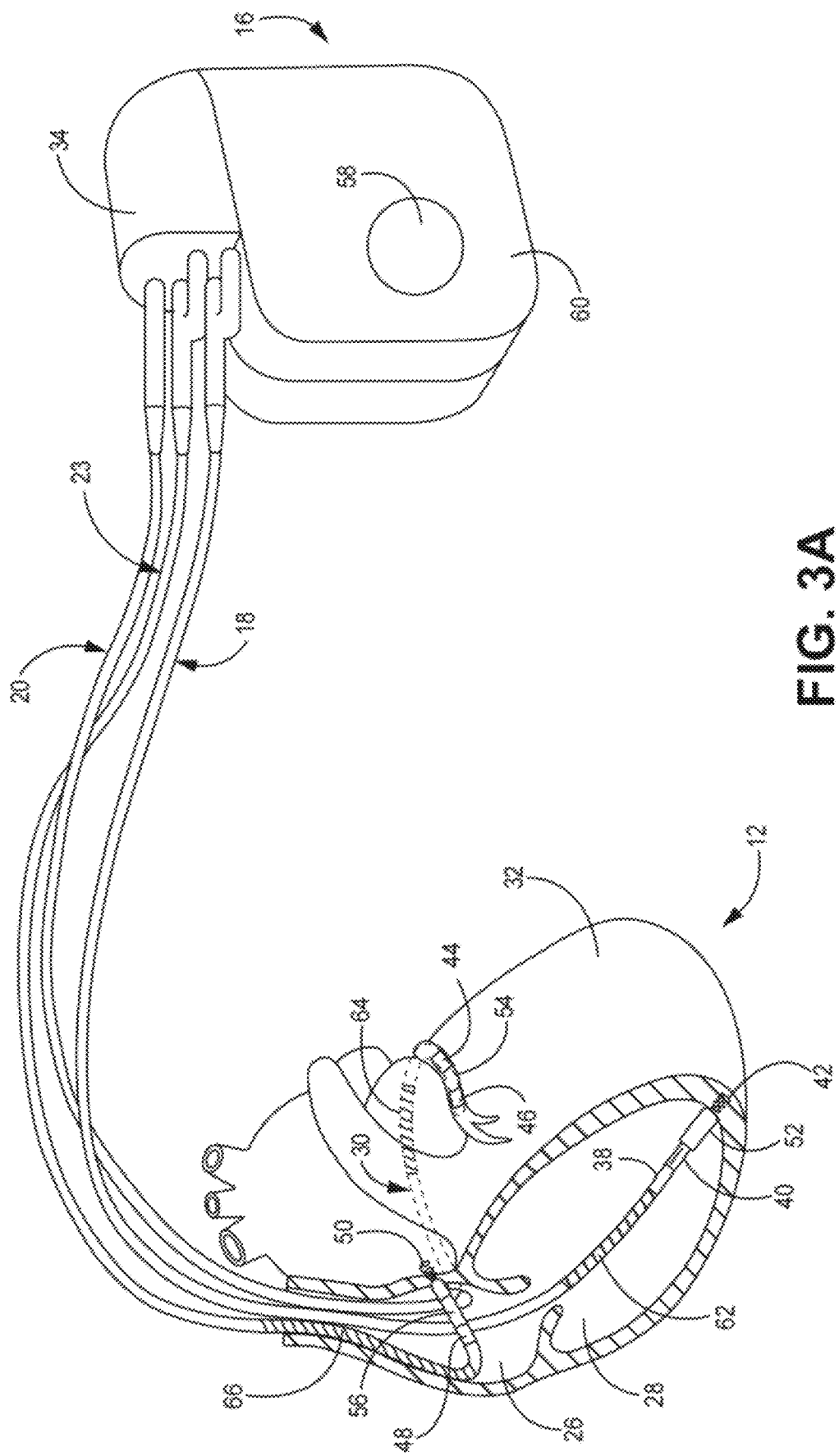
FIG. 3A is a conceptual diagram illustrating an example therapy system (e.g., dual-chamber implantable medical device) that is configured to provide therapy to a heart of patient suffering from atrial fibrillation through a His-bundle or bundle-branch pacing lead and lead placed in the left ventricle using an IMD.

FIG. 3A is a conceptual diagram illustrating IMD 16 and leads 18, 20, 23 of therapy system 10 in greater detail. The triple chamber IMD 16 may be used for cardiac rhythm therapy and defibrillation or cardioversion therapy (CRT-D). Leads 18, 20, 23 may be electrically coupled to a stimulation generator, a sensing module, or other modules of IMD 16 via connector block 34. In some examples, proximal ends of leads 18, 20, 23 may include electrical contacts that electrically couple to respective electrical contacts within connector block 34. In addition, in some examples, leads 18, 20, 23 may be mechanically coupled to connector block 34 with the aid of set screws, connection pins, or another suitable mechanical coupling mechanism.

Each of the leads 18, 20, 23 includes an elongated, insulative lead body, which may carry any number of concentric coiled conductors separated from one another by tubular, insulative sheaths. In the illustrated example, an optional pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 23. In FIG. 3A, pressure sensor 38 is disposed in right ventricle 28. Pressure sensor 38 may respond to an absolute pressure inside right ventricle 28, and may be, for example, a capacitive or piezoelectric absolute pressure sensor. In other examples, pressure sensor 38 may be positioned within other regions of heart 12 and may monitor pressure within one or more of the other regions of heart 12, or pressure sensor 38 may be positioned elsewhere within or proximate to the cardiovascular system of patient 14 to monitor cardiovascular pressure associated with mechanical contraction of the heart. Optionally, a pressure sensor in the pulmonary artery can be used that is in communication with IMD 16.

Electrodes 40, 44 and 48 may take the form of ring electrodes, and electrodes 42, 46 and 50 may take the form of extendable and/or fixed helix tip electrodes mounted within insulative electrode heads 52, 54 and 56, respectively. Each of electrodes 40, 42, 44, 46, 48 and 50 may be electrically coupled to a respective one of the coiled conductors within the lead body of its associated lead 18, 20, 23, and thereby coupled to respective ones of the electrical contacts on the proximal end of leads 18, 20 23.

Figure 3B:
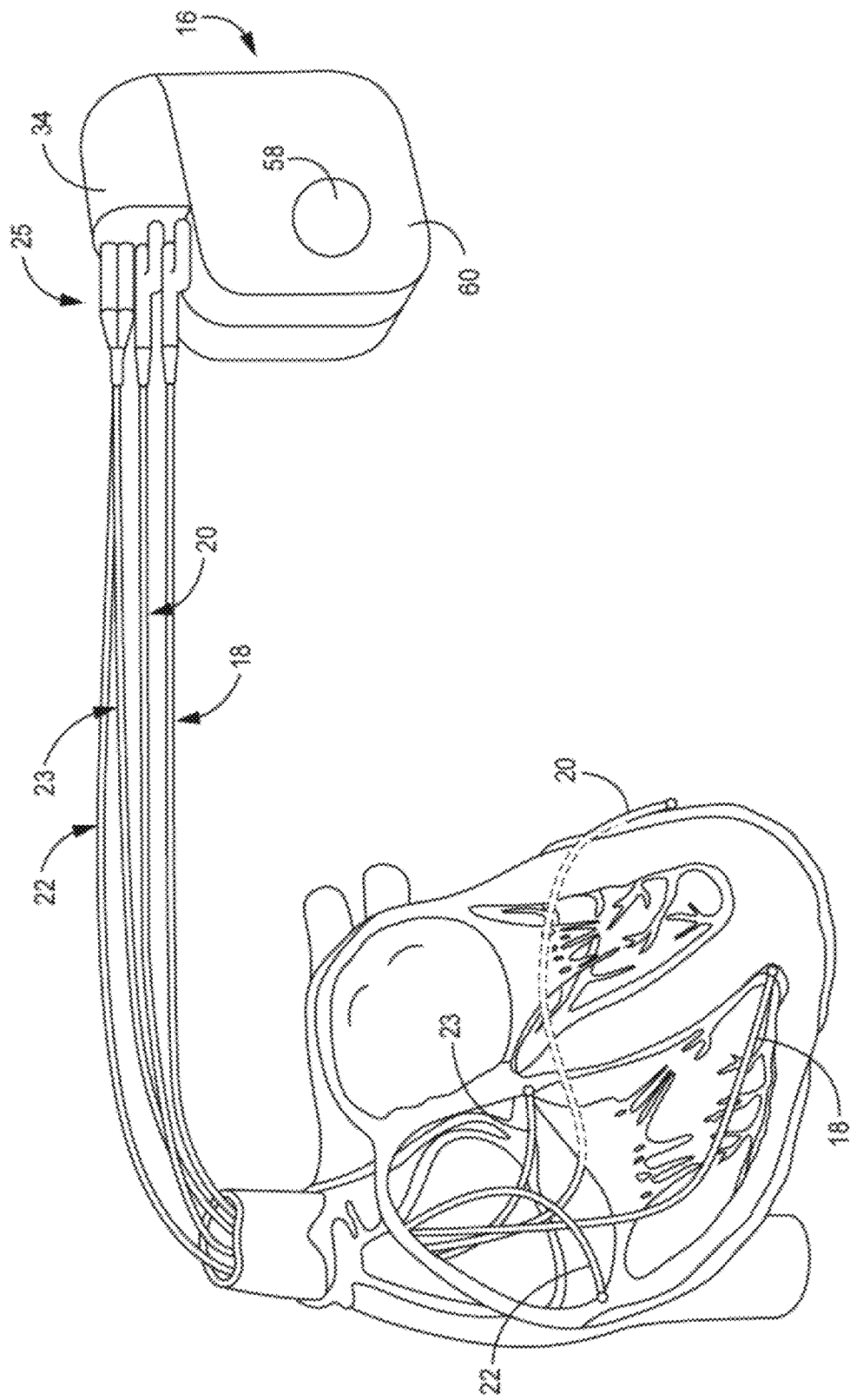
FIG. 3B is a schematic diagram illustrating an example of a His-bundle or bundle-branch pacing lead positioned in bundle of the His in a cross-sectional view of the heart using an 1 MB.

Electrodes 40, 42, 44, 46, 48 and 50 may sense electrical signals attendant to the depolarization and repolarization of heart 12. The electrical signals are conducted to IMD 16 via the respective leads 18, 20, 23. In some examples, IMD 16 also delivers pacing pulses via electrodes 40, 42, 44, 46, 48, 50 to cause depolarization of cardiac tissue of heart 12. In some examples, as illustrated in FIGS. 3A-B, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 may be defined by an uninsulated portion of an outward facing portion of housing 60 of IMD 16. Electrode 50 may be used for pacing and/or sensing of the His bundle or bundle branch tissue. Other divisions between insulated and uninsulated portions of housing 60 may be employed to define two or more housing electrodes. In some examples, housing electrode 58 includes substantially all of housing 60. Any of the electrodes 40, 42, 44, 46, 48 and 50 may be used for unipolar sensing or pacing in combination with housing electrode 58 or for bipolar sensing with two electrodes in the same pacing lead. In one or more embodiments, housing 60 may enclose a stimulation generator (see FIG. 5) that generates cardiac pacing pulses and defibrillation or cardioversion shocks, as well as a sensing module for monitoring the patient's heart rhythm.

Leads 18, 20, 23 may also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Pressure sensor 38 may be coupled to one or more coiled conductors within lead 18. In FIG. 3A, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 23 in other examples, or to a lead other than leads 18, 20, 23 carrying stimulation and sense electrodes. In addition, in some examples, pressure sensor 38 may be self-contained device that is implanted within heart 12, such as within the septum separating right ventricle 28 from left ventricle 32, or the septum separating right atrium 26 from left atrium 33. In such an example, pressure sensor 38 may wirelessly communicate with IMD 16.

FIG. 3B shows IMD 16 coupled to leads 18, 20, 22, 23. Right atrial (RA) lead 22 may extend through one or more veins and the vena cava, and into the right atrium 26 of heart 12. RA lead 22 may be connected to triple chamber IMD 16, e.g., using a Y-adaptor. IMD 16 may be used for cardiac rhythm therapy and defibrillation or cardioversion therapy (CRT-D). RA lead 22 may include electrodes that are the same or similar to the electrodes of lead 18, 20, 23, such as ring electrodes 40, 44 and 48, extendable helix tip electrodes 42, 46 and 50, and/or elongated electrodes 62, 64, 66, in the form of a coil.

The configuration of therapy system 10 illustrated in FIGS. 2A-4 are merely examples. In other examples, a therapy system may include epicardial leads and/or patch electrodes instead of or in addition to the transvenous leads 18, 20, 22 and/or cardiac conduction system pacing lead 23 illustrated in FIGS. 2A-4 or other configurations shown or described herein or incorporated by reference. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, such therapy systems may include any suitable number of leads coupled to IMD 16, and each of the leads may extend to any location within or proximate to heart 12. For example, other examples of therapy systems may include three transvenous leads located as illustrated in FIGS. 2A-4, and an additional lead located within or proximate to left atrium 33 (FIG. 1). As another example, other examples of therapy systems may include a single lead that extends from IMD 16 into right atrium 26 or right ventricle 28, or two leads that extend into a respective one of right ventricle 28 and right atrium 26. An example of this type of therapy system is shown in FIGS. 3A-3B. If four leads are required for therapy delivery, an IS-1 connector may be used in conjunction with Y-adaptor 25 extending from the RA port of the connector. The Y-adaptor allows two separate leads—e.g., right atrial lead and the bundle pacing bundle lead—to extend from the two separate legs of the "Y shape" while the single leg is inserted into connector block 34 on IMD 16.

Figure 4:
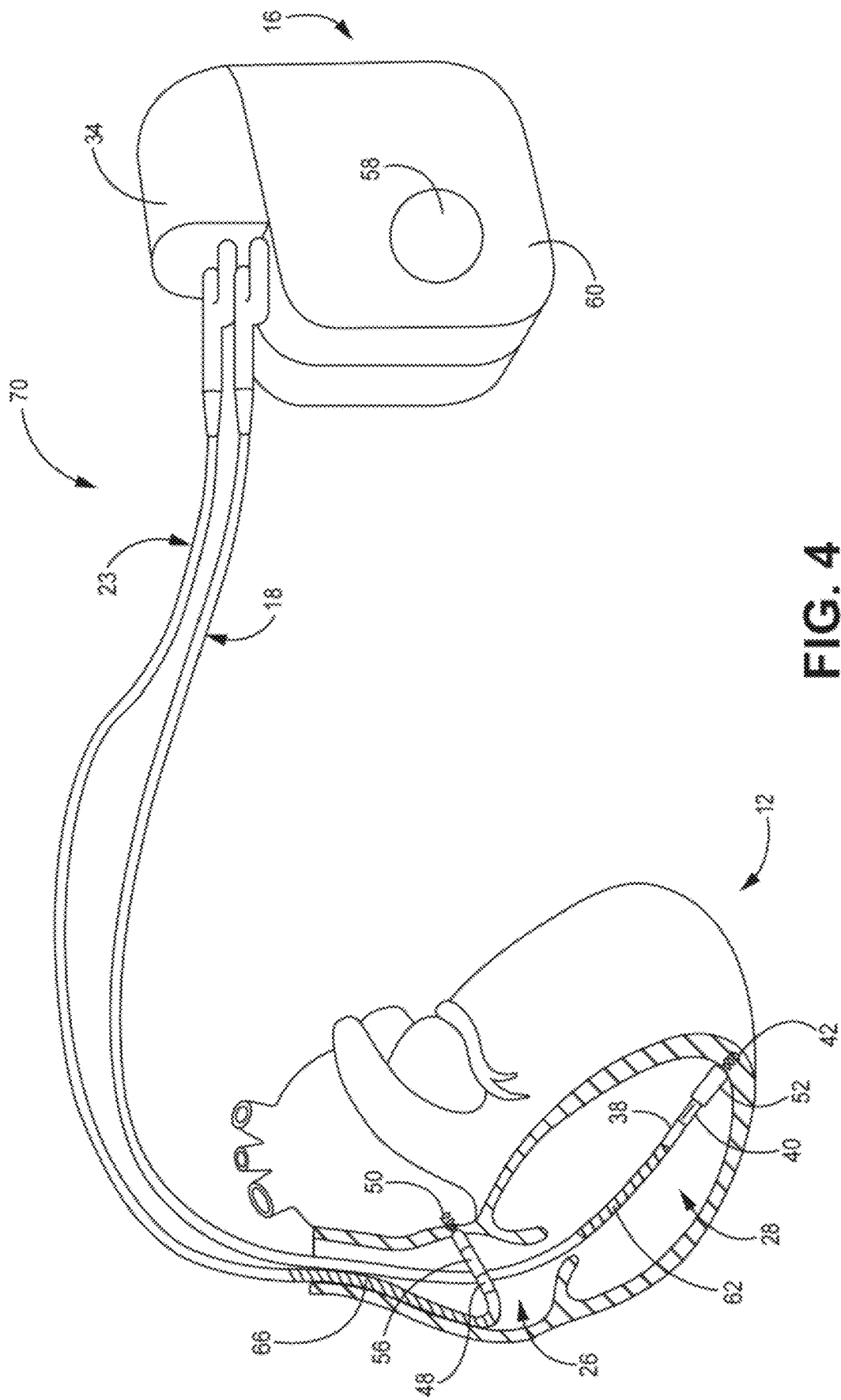
FIG. 4 is a conceptual diagram illustrating an example of a therapy system (e.g., dual chamber implantable medical device) that is configured to provide therapy to a heart of patient through a His-bundle or bundle-branch pacing lead and lead placed in the left ventricle using an IMD.

FIG. 4 is a conceptual diagram illustrating another example of therapy system 70. Therapy system 70 shown in FIG. 4 may be useful for providing defibrillation and pacing pulses to heart 12. Therapy system 70 is similar to therapy system 10 of FIGS. 2A-B or 3A-B, but includes two leads 18, 23, rather than three leads. Therapy system 70 may utilize an IMD 16 configured to deliver, or perform, dual chamber pacing. Leads 18, 23 are implanted within right ventricle 28 and right atrium 26 to pace one or more portions of the cardiac conduction system such as the His bundle or one or both bundle branches, respectively.

Cardiac conduction system pacing lead 23 may be in the form of a helix (also referred to as a helical electrode) may be positioned proximate to, near, adjacent to, or in, area or portions of the cardiac conduction system such as, e.g., ventricular septum, triangle of Koch, the His bundle, left right bundle branch tissues, and/or right bundle branch tissue. Cardiac conduction system pacing lead 23 may be configured as a bipolar lead or as a quadripolar lead that may be used with a pacemaker device, a CRT-P device or a CRT-ICD.

Figure 5:
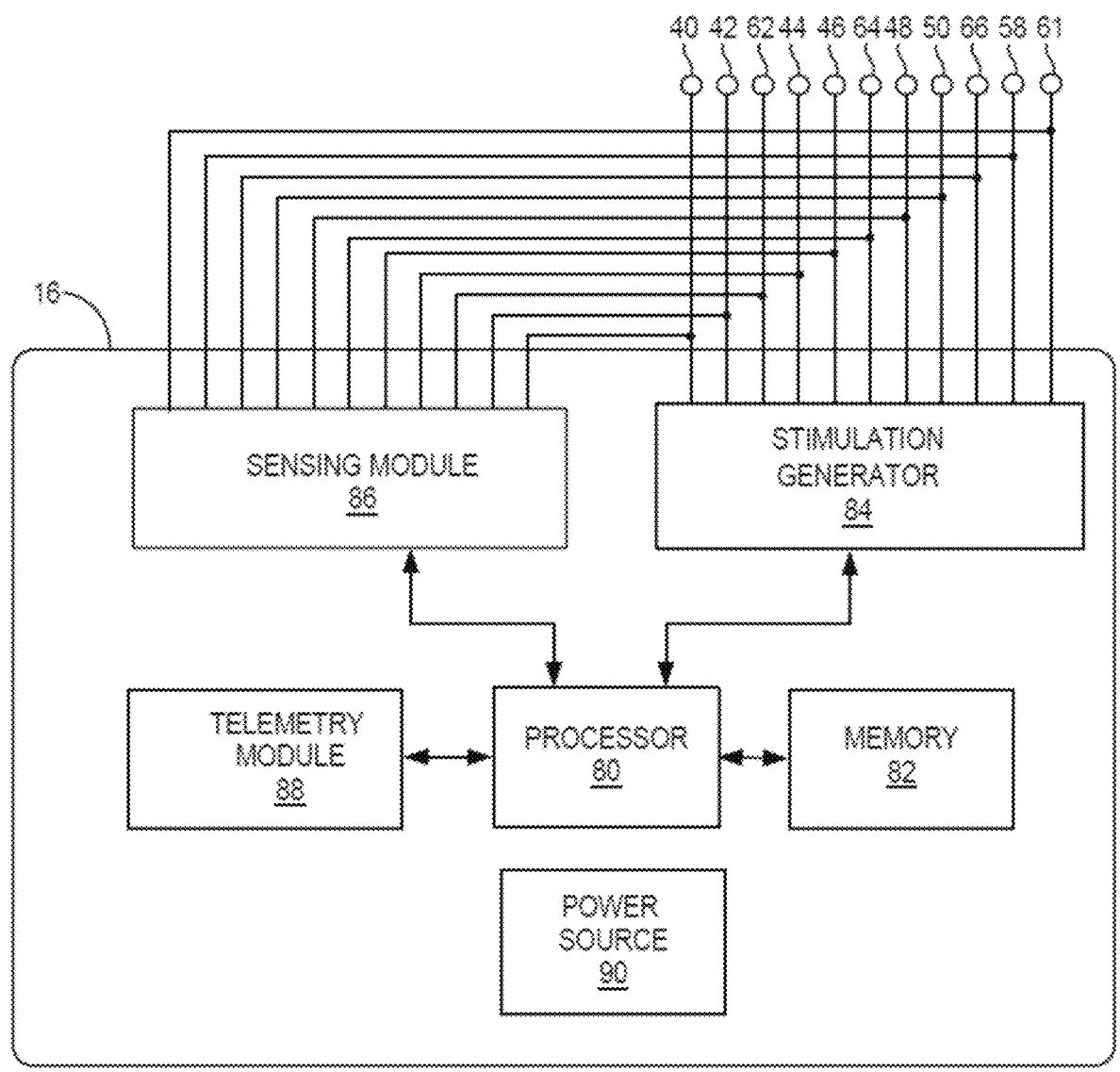
FIG. 5 is a functional block diagram illustrating an example of a configuration of an implantable medical device of FIGS. 2A and 3A-4.

FIG. 5 is a functional block diagram of one example configuration of IMD 16, which includes processor 80, memory 82, stimulation generator 84 (e.g., electrical pulse generator or signal generating circuit), sensing module 86 (e.g., sensing circuit), telemetry module 88, and power source 90. One or more components of IMD 16, such as processor 80, may be contained within a housing of IMD 16 (e.g., within a housing of a pacemaker). Telemetry module 88, sensing module 86, or both telemetry module 88 and sensing module 86 may be included in a communication interface. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs (e.g., optimization of the AV delay, VV delay, VV delay etc.), which may be stored in memory 82. Specifically, processor 80 may control stimulation generator 84 to deliver electrical pulses with amplitudes, pulse widths, frequency, or electrode polarities specified by the selected one or more therapy programs.

In some embodiments, RA lead 22 may be operably coupled to electrode 61, which may be used to monitor or pace the RA. Stimulation generator 84 may be electrically coupled to electrodes 40, 42, 44, 46, 48, 50, 58, 61, 62, 64, and 66, e.g., via conductors of respective lead 18, 20, 22, 23 or, in the case of housing electrode 58, via an electrical conductor disposed within housing 60 of IMD 16. Stimulation generator 84 may be configured to generate and deliver electrical stimulation therapy to heart 12. For example, stimulation generator 84 may deliver defibrillation shocks to heart 12 via at least two of electrodes 58, 62, 64, 66. Stimulation generator 84 may deliver pacing pulses via ring electrodes 40, 44, 48 coupled to leads 18, 20, 23, respectively, and/or helical electrodes 42, 46, and 50 of leads 18, 20, or 23, respectively. Cardiac conduction system pacing therapy can be delivered through cardiac conduction system lead 23 that is connected to an atrial, RV, or LV connection port of connector block 34. In some embodiments, the cardiac conduction system pacing therapy can be delivered through leads 18 and/or 23. In some examples, stimulation generator 84 delivers pacing, cardioversion, or defibrillation stimulation in the form of electrical pulses. In other examples, stimulation generator 84 may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation shocks or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 61, 62, 64 or 66 in order to monitor electrical activity of heart 12, e.g., via electrical signals, such as electrocardiogram (ECG) signals and/or electrograms (EGMs). Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may include an amplifier. In response to the signals from processor 80, the switch module may couple the outputs from the selected electrodes to one of the sensing channels.

In some examples, one channel of sensing module 86 may include an R-wave amplifier that receives signals from electrodes 40, 42, which are used for pacing and sensing in right ventricle 28 of heart 12. Another channel may include another R-wave amplifier that receives signals from electrodes 44, 46, which are used for pacing and sensing proximate to left ventricle 32 of heart 12. In some examples, the R-wave amplifiers may take the form of an automatic gain-controlled amplifier that provides an adjustable sensing threshold as a function of the measured R-wave amplitude of the heart rhythm.

In addition, in some examples, one channel of sensing module 86 may include a P-wave amplifier that receives signals from electrodes 48, 50, which are used for pacing and sensing in right atrium 26 of heart 12. In some examples, the P-wave amplifier may take the form of an automatic gain-controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that includes an amplifier with a relatively wider pass band than the R-wave or P-wave amplifiers or a high-resolution amplifier with relatively narrow-pass band for His bundle or bundle branch potential recording. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may include a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking time period and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module may also determine the amplitude of the cardiac pacing pulses.

During pacing, escape interval counters within the pacer timing/control module may be reset upon sensing of R-waves and P-waves. Stimulation generator 84 may include pacer output circuits that are coupled, e.g., selectively by a switching module, to any combination of electrodes 40, 42, 44, 46, 48, 50, 58, 61, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

Telemetry module 88 includes any suitable hardware, firmware, software or any combination thereof for communicating with another device, such as programmer 24 (FIG. 2A). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

The illustrative devices and methods described herein may provide adaptive cardiac conduction system pacing therapy. The illustrative adaptive cardiac conduction system pacing therapy may provide configuration of the timing of the cardiac conduction system pacing as well as timing for traditional left ventricular pacing when used in conjunction with the cardiac conduction system pacing therapy. Additionally, the illustrative adaptive cardiac conduction pacing therapy may also provide switching from cardiac conduction system pacing therapy only to a combination of cardiac conduction system pacing therapy and traditional left ventricular pacing therapy.

Figure 6:
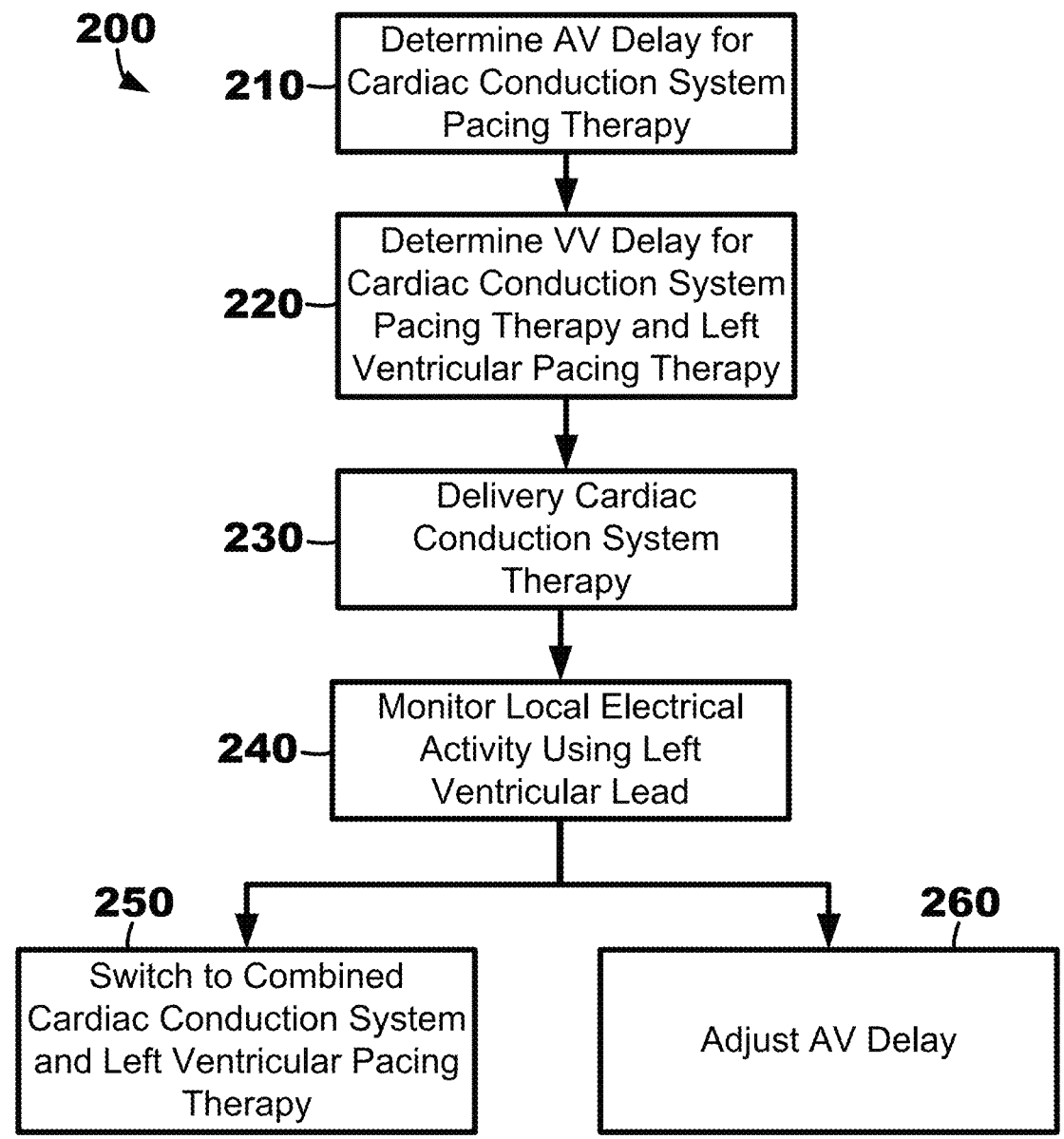
FIG. 6 is a block diagram of an illustrative method of adaptive cardiac conduction system pacing therapy that may be utilized by the devices of FIGS. 1-5.

An illustrative method 200 of adaptive cardiac conduction system pacing therapy that may be utilized by the devices of FIGS. 1-5 is depicted in FIG. 6. As shown, the method 200 may determine a paced AV delay 210 for use in delivery of cardiac conduction system pacing therapy using the cardiac conduction system electrode. The paced AV delay is a time period between a sensed or paced atrial event (e.g., depolarization of the atrium, p-wave in an electrocardiogram, etc.) and delivery of cardiac conduction system pacing therapy (e.g., delivery of a pacing pulse to the cardiac conduction system).

Figure 7:
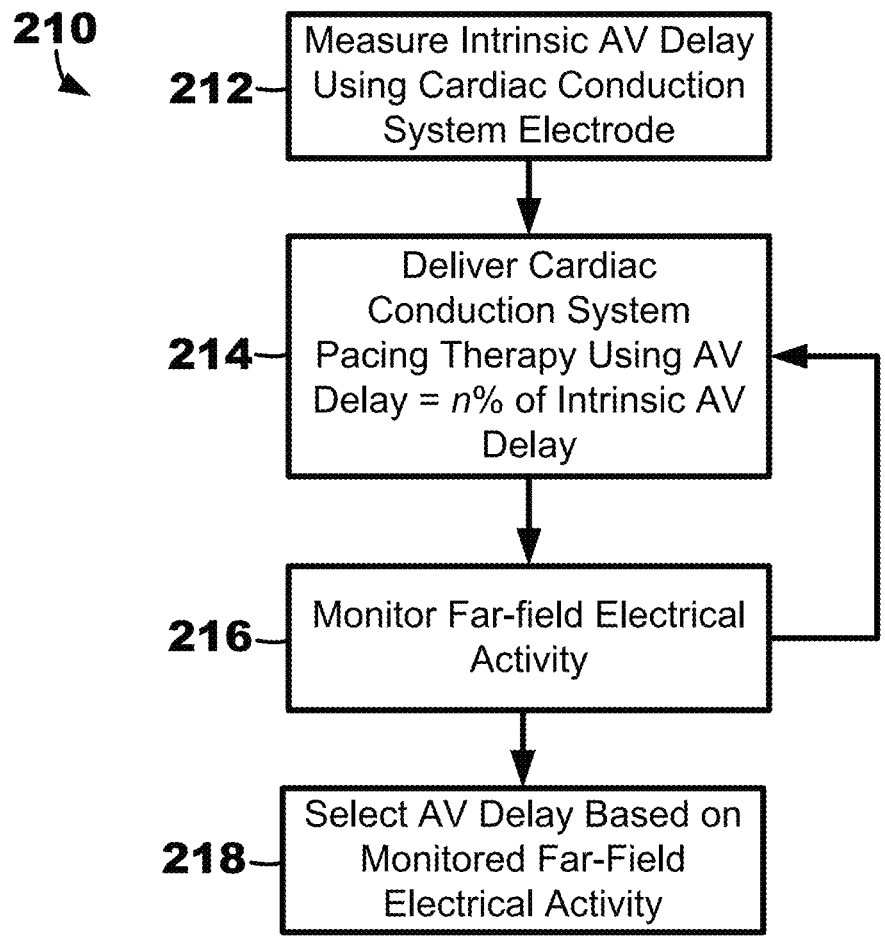
FIG. 7 is a block diagram of an illustrative process of determining an AV delay of the method of FIG. 6.

The paced AV delay may be determined using various illustrative processes. One illustrative process of determining AV delay 210 of the method of FIG. 6 is depicted in FIG. 7. The process 210 of FIG. 7 may include measuring an intrinsic AV delay using a cardiac conduction system electrode 212. The cardiac conduction system electrode is the electrode configured to deliver cardiac conduction system (for example, an electrode positioned on cardiac conduction system lead 23 as described herein). The intrinsic AV delay is a time period between a sensed intrinsic, or naturally-occurring, atrial event (e.g., depolarization of the atrium, p-wave in an electrocardiogram, etc.) and a sensed intrinsic, or naturally-occurring, ventricular event (e.g., depolarization of the left ventricle or both ventricles, r-wave in an electrocardiogram, etc.).

The measured intrinsic AV delay may be used when testing various paced AV delays. For example, the process 210 may include delivering cardiac conduction system pacing therapy to the patient's cardiac conduction system using the cardiac conduction system electrode at a plurality of different paced AV delays that are less than the intrinsic AV delay 214. In this example, the plurality of different paced AV delays may be based on various percentages of the intrinsic AV delay. Each various percentage may be referred to an AV delay percentage. For instance, the plurality of different paced AV delays may be between about 20% of the intrinsic AV delay and about 90% of the intrinsic AV delay. For example, the plurality of different paced AV delays may include a range of paced AV delays based on different AV delay percentages spaced 5% or more apart from one another. In at least one embodiment, the plurality of different paced AV delays may include 20% of the intrinsic AV delay, 30% of the intrinsic AV delay, 40% of the intrinsic AV delay, 50% of the intrinsic AV delay, 60% of the intrinsic AV delay, 70% of the intrinsic AV delay, and 80% of the intrinsic AV delay.

The cardiac conduction system pacing therapy may be delivered for one or a plurality of cardiac cycles at each different paced AV delay (or each different AV delay percentage) to, e.g., provide an appropriate sample size of data to evaluate. The process 210 may further monitor far-field electrical activity 216 during delivery of the cardiac conduction system pacing therapy. The far-field electrical activity may be monitored by any electrode positioned outside of the cardiac conduction system pacing therapy area of interest. In at least one embodiment, the far-field electrical activity may be monitored by a ring electrode positioned on a left ventricular lead located in the coronary sinus. In at least one embodiment, the far-field electrical activity may be monitored by an external electrode disposed on the skin of the patient's torso.

Then, a paced AV delay of the plurality of different paced AV delays may be selected 218 based on the far-field electrical activity monitored during the delivery of cardiac conduction system pacing therapy at the plurality of different paced AV delays. More specifically, one or more metrics may be derived or determined from the far-field electrical activity that may be used to determine the most effective or optimal paced AV delay for the cardiac conduction system pacing therapy. In at least one embodiment, a time period between the delivery of the cardiac conduction system pacing therapy and an end of ventricular depolarization (e.g., QRS offset) may be determined for each of the plurality of different paced AV delays. Then, the paced AV delay or AV delay percentage providing the shortest time period between the delivery of the cardiac conduction system pacing therapy and an end of ventricular depolarization may be selected.

As noted herein, it is to be understood that the selected paced AV delay may be percentage of the intrinsic AV delay, which may be referred to as an AV delay percentage. For example, the selected AV delay percentage may be 70% of the intrinsic AV delay. In this way, the intrinsic AV delay may be measured periodically by halting any cardiac pacing therapy, and the paced AV delay may be adjusted accordingly according the selected AV delay percentage.

Thus, the process 210 may result in a selected AV delay for delivery of cardiac conduction system pacing therapy. The method 200 may further include determining a VV delay for cardiac conduction system and left ventricular pacing therapy 220. The VV delay may be the time period between the delivery of the cardiac conduction system pacing therapy and the delivery of the left ventricular pacing therapy.

Figure 8:
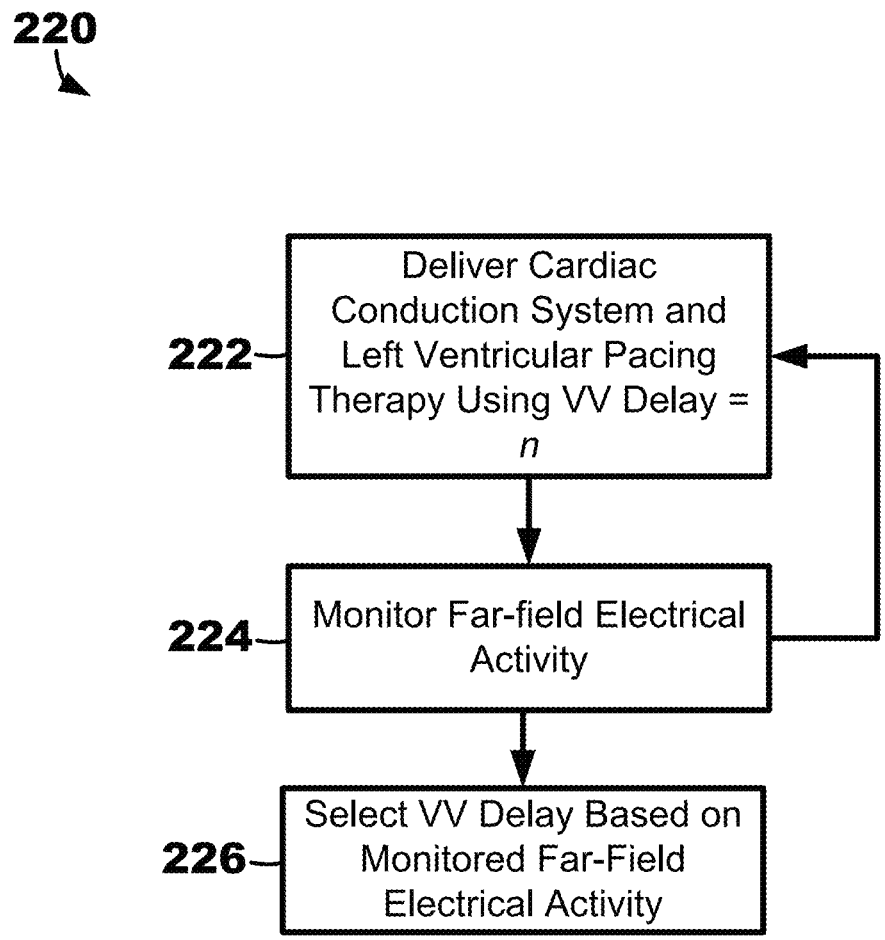
FIG. 8 is a block diagram of an illustrative process of determining a VV delay of the method of FIG. 6.

The paced VV delay may be determined 220 using various illustrative processes. One illustrative process of determining VV delay 220 of the method of FIG. 6 is depicted in FIG. 8. The process 220 of FIG. 8 may deliver cardiac conduction system pacing therapy to the patient's cardiac conduction system at the selected AV delay and delivering left ventricular pacing therapy at a plurality of different paced VV delays 222. In this example, the plurality of different paced VV delays may include a range of different time values. For instance, the plurality of different paced VV delays may be between about −80 milliseconds (ms) to about 80 ms. In other words, the left ventricular pacing may be delivered between about 80 ms before the delivery of the cardiac conduction system pacing therapy to about 80 ms after the delivery of the cardiac conduction system pacing therapy. For example, the plurality of different paced VV delays may include a range of paced VV delays spaced apart from one another by a selected interval such as 10 ms. In at least one embodiment, the plurality of different paced VV delays may include −60 ms, −40 ms, −20 ms, 0 ms, 20 ms, 40 ms, and 60 ms.

Further, the cardiac conduction system pacing therapy and left ventricular pacing therapy may be delivered 222 for one or a plurality of cardiac cycles at each different paced VV delay to, e.g., provide an appropriate sample size of data to evaluate. The process 220 may further monitoring far-field electrical activity 224 during delivery of the cardiac conduction system and left ventricular pacing therapy. The far-field electrical activity may be monitored by any electrode positioned outside of the cardiac conduction system pacing therapy area of interest. In at least one embodiment, the far-field electrical activity may be monitored by a ring electrode positioned on a left ventricular lead located in the coronary sinus. In at least one embodiment, the far-field electrical activity may be monitored by an external electrode disposed on the skin of the patient's torso.

Then, a paced VV delay of the plurality of different paced VV delays may be selected 226 based on the far-field electrical activity monitored during the delivery of cardiac conduction system pacing therapy and left ventricular pacing therapy at the plurality of different paced VV delays. More specifically, one or more metrics may be derived or determined from the far-field electrical activity that may be used to determine the most effective or optimal paced VV delay for the cardiac conduction system and left ventricular pacing therapy. In at least one embodiment, the time period between the earliest pacing (e.g., either cardiac conduction system pacing therapy or left ventricular pacing therapy depending on the present VV delay) and an end of ventricular depolarization (e.g., QRS duration, the time period between QRS onset and QRS offset, etc.) may be determined for each of the plurality of different paced VV delays. Then, the paced VV delay providing the shortest, or narrowest, time period between pacing and the end of ventricular depolarization (e.g., QRS duration) may be selected.

Thus, the process 220 may result in a selected VV delay for delivery of cardiac conduction system and left ventricular pacing therapy when used in combination. As a result, the method 200 may then be configured to deliver cardiac conduction system pacing therapy and combined cardiac conduction system and left ventricular pacing therapy, if needed. Thus, the method 200 may initiate or begin delivery of cardiac conduction system pacing therapy alone 230 and monitoring local electrical activity of the patient using a left ventricular electrode 240 during the delivery of cardiac conduction system pacing therapy. The local electrical activity may be used to determine whether to switch to combined cardiac conduction system and left ventricular pacing therapy 250. For example, various metrics may be derived or generated from the local electrical activity, which may then be used to determine whether to switch to combined cardiac conduction system and left ventricular pacing therapy 250.

Figure 9:
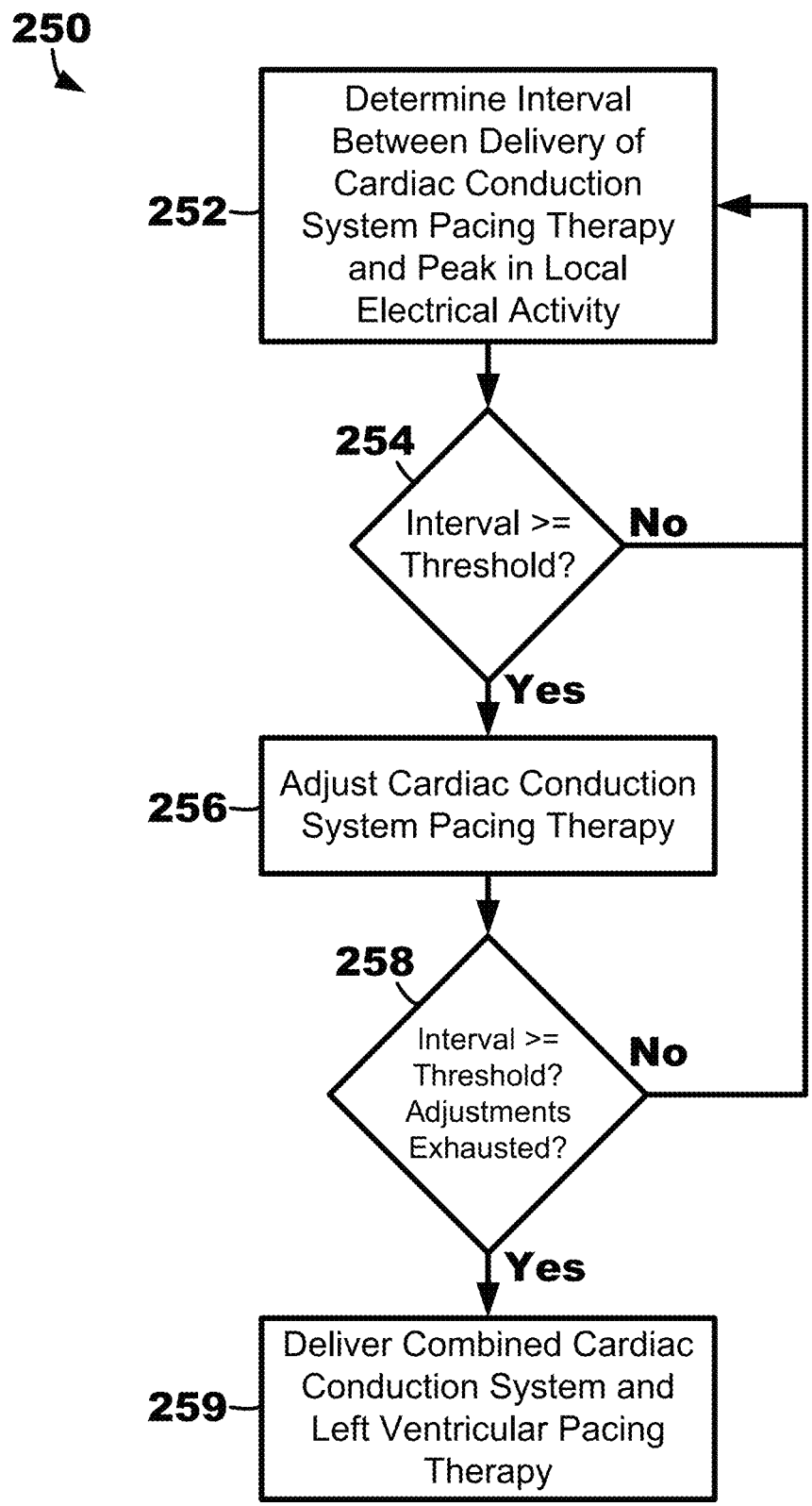
FIG. 9 is a block diagram of an illustrative process of switching to combined cardiac conduction system and left ventricular pacing therapy of the method of FIG. 6.

An illustrative process 250 of switching to combined cardiac conduction system and left ventricular pacing therapy of the method of FIG. 6 is depicted in FIG. 9. The process 250 includes determining an interval between the delivery of cardiac conduction system pacing therapy and a peak in the local monitored local activity 252 and then comparing the interval to a threshold value 254. The threshold value may be between about 25 ms and about 75 ms. In at least one embodiment, the threshold value is 50 ms. In other embodiments, the threshold value may be greater than or equal to 25 ms, greater than or equal to 35 ms, greater than or equal to 45 ms, greater than or equal to 55 ms, etc. and/or less than or equal to 75 ms, less than or equal to 65 ms, less than or equal to 50 ms, etc. If the measured interval is greater than or equal to the threshold value, then it may be determined that the cardiac conduction system pacing therapy may be less than optimal or most effective, and thus may be adjusted and/or may benefit from the additional of left ventricular pacing therapy. If the measured interval is less than the threshold value, then it may be determined that the cardiac conduction system pacing therapy is effective and the process may return to monitoring the local electrical activity 252.

As shown in process 250 of FIG. 9, the cardiac conduction system pacing therapy may be adjusted 256 if the interval is greater than or equal to the threshold. For example, the cardiac conduction system pacing output may be increased (e.g., amplitude or voltage may be increased, pacing burst lengthened, pacing frequency increased, number of bursts per pulse increased, etc.). Further, for example, the electrode vector of cardiac conduction system pacing therapy may be changed (e.g., increase the number of electrodes used to deliver cardiac conduction system pacing therapy, change to different electrodes or a different electrode combination being used to deliver cardiac conduction system pacing therapy). Simultaneously, the process 250 may continue monitoring the local electrical activity 252 and comparing the interval to the threshold 258, and if the interval becomes less than the threshold, then the process 250 may return to delivering cardiac conduction system pacing therapy at the newly-adjusted pacing output and monitoring local electrical activity.

If adjustment of a cardiac conduction system pacing therapy output parameter does not result in the interval being less than the threshold, the process 250 may continue looping to adjust the output parameter until the adjustments are exhausted 258. The pacing output parameter adjustments may be exhausted when the pacing output cannot be further adjusted or increased. In other words, the cardiac conduction system pacing output may be exhausted when it is at its upper, or maximum, limit. When the adjustments are exhausted, the process 250 may proceed to delivering combined cardiac conduction system and left ventricular pacing therapy 259 according to the previously-determined AV delay and VV delay. Thus, the process 250 may switch from cardiac conduction system pacing therapy only to cardiac conduction system pacing therapy being used in conjunction with left ventricular pacing therapy.

The method 200 further includes adjusting the paced AV delay 260, e.g., periodically, based on measuring the intrinsic AV delay in the absence of delivery of pacing therapy and using the previously-determined AV delay percentage to determine the new paced AV delay.

The illustrative devices and methods described herein may be further configured to determine whether cardiac conduction system pacing therapy being delivered to the patient's cardiac conduction system has selectively or non-selectively captured the patient's cardiac conduction system. Cardiac conduction system pacing therapy having selective capture of the cardiac conduction system may be defined as pacing therapy that delivers pacing therapy only to the cardiac conduction system and that does not deliver pacing therapy directly to myocardial or muscular cardiac tissue. In other words, selective cardiac conduction system pacing therapy paces the cardiac conduction system alone. Cardiac conduction system pacing therapy having non-selective capture of the cardiac conduction system may be defined as pacing therapy that delivers pacing therapy to the cardiac conduction system and also directly to the myocardial or muscular cardiac tissue. In other words, non-selective cardiac conduction system pacing therapy paces both the cardiac conduction system and myocardial or muscular cardiac tissue. The illustrative devices and methods, using a near-field signal, may be able to determine whether the delivered cardiac conduction system pacing therapy is selective or non-selective, which may be helpful in delivery of effective cardiac therapy to a patient.

Figure 10:
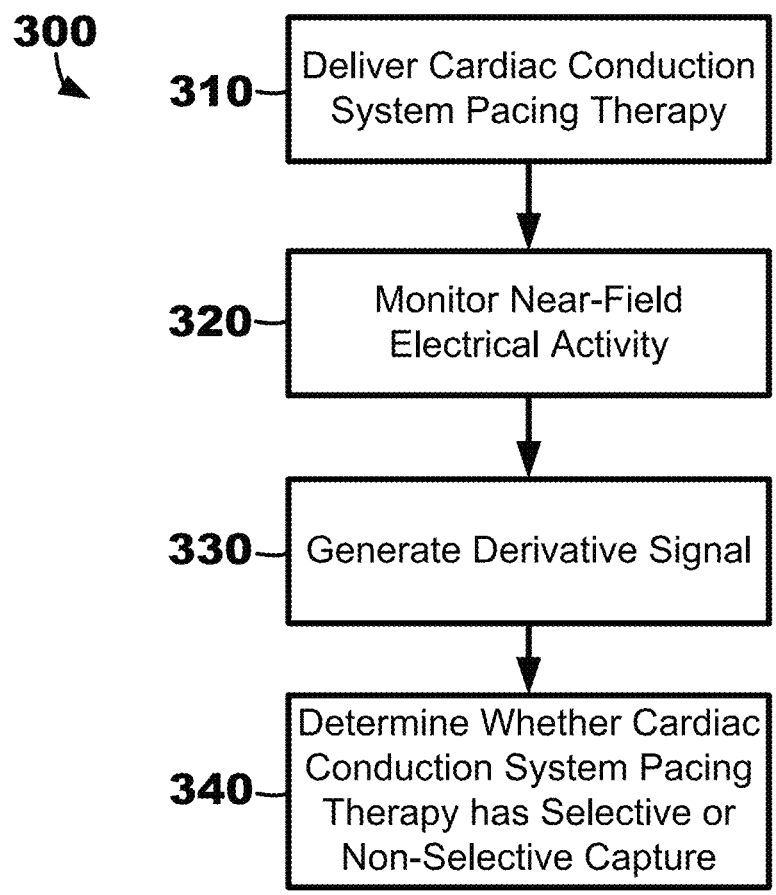
FIG. 10 is a block diagram of an illustrative method of determining whether cardiac conduction system pacing therapy has selectively captured the cardiac conduction system.

An illustrative method 300 of determining whether cardiac conduction system pacing therapy has selectively captured the cardiac conduction system is depicted in FIG. 10. The method 300 may include delivering cardiac conduction system pacing therapy 310 using, for example, one of the illustrative devices described herein with respect to FIGS. 1-5, and monitoring near-field electrical activity 320 during delivery of the cardiac conduction system pacing therapy. The near-field electrical activity may be monitored via one or more implantable electrodes that are located proximate the left bundle branch.

The near-field electrical activity 320 may be monitored for a sensing time period following the delivery of the cardiac conduction system pacing therapy. The sensing time period may be between about 25 ms and about 150 ms. In at least one embodiment, the sensing time period is 50 ms. In other embodiments, the sensing time period may be greater than or equal to 25 ms, greater than or equal to 35 ms, greater than or equal to 45 ms, greater than or equal to 55 ms, greater than or equal to 65 ms, etc. and/or less than or equal to 150 ms, less than or equal to 125 ms, less than or equal to 100 ms, less than or equal to 75 ms, less than or equal to 55 ms, etc.

Additionally, the sensing time period may follow a blanking time period following the delivery of the cardiac conduction system pacing therapy. The blanking time period may be between about 5 ms and about 30 ms. In at least one embodiment, the blanking time period is 20 ms. In other embodiments, the blanking time period may be greater than or equal to 5 ms, greater than or equal to 10 ms, greater than or equal to 15 ms, etc. and/or less than or equal to 30 ms, less than or equal to 25 ms, less than or equal to 17 ms, etc.

In other words, following the delivery of the cardiac conduction system pacing therapy, a blanking time period, which may be 20 ms, may delay the measuring or monitoring of the near-field electrical activity that may then be measured or monitored for a sensing time period, which may be 50 ms.

A derivative signal may be generated 330 based on the monitored near-field electrical activity during the sensing time period. The derivative signal may be described as computing a derivative of the near-field electrical signal (e.g., electrocardiogram) by taking differences of successive samples. In at least one embodiment, a 5-point derivative of the near-field signal is generated, e.g., so as to provide a smoother derivative signal and mute the chances of large changes due to local artifacts.

The method 300 may then determine whether the pacing therapy has selective or non-selective capture of the cardiac conduction system based on the derivative signal 340. Determining whether the pacing therapy has selective or non-selective capture of the cardiac conduction system based on the derivative signal may be performed, or executed, a variety of different ways and using a variety of different metrics. An illustrative process 340 of determining whether cardiac conduction system pacing therapy has selectively or non-selectively captured the cardiac conduction system is depicted in FIG. 11.

Figure 11:
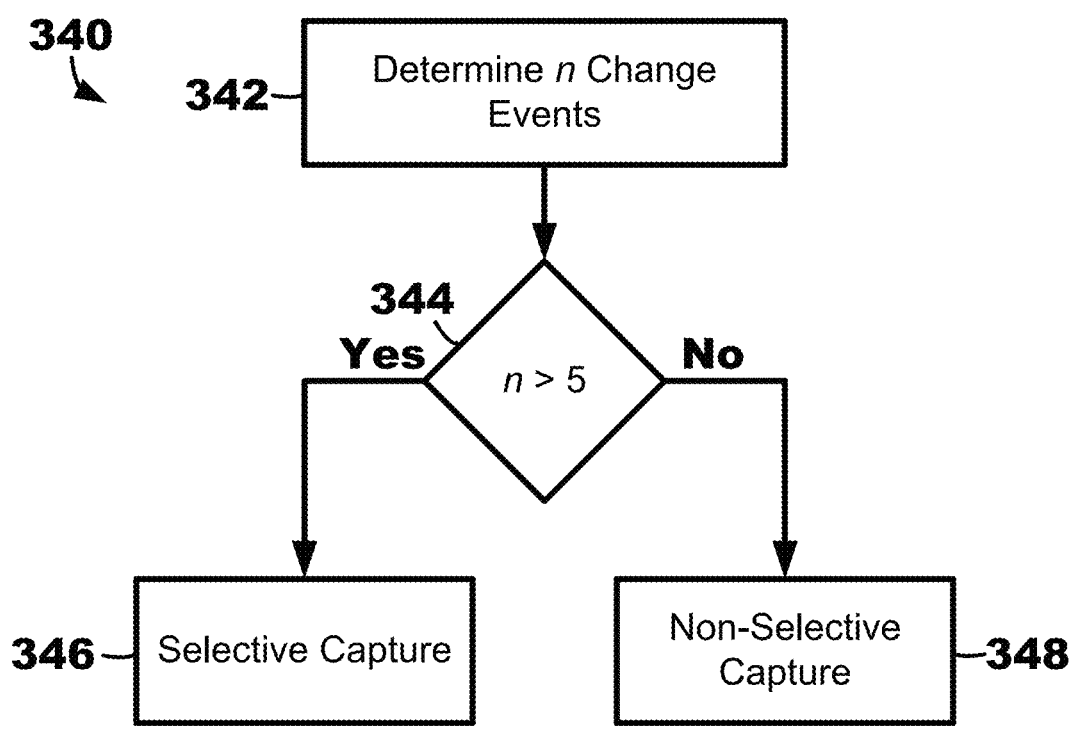
FIG. 11 is a block diagram of an illustrative process of determining whether cardiac conduction system pacing therapy has selectively or non-selectively captured the cardiac conduction system.

As shown in FIG. 11, a number of change events within the derivative signal over the sensing period may be determined 342 and then compared to a change event threshold 344. In this example, the change event threshold is 5. Thus, if more than 5 change events occur within the derivative signal over the sensing period, then it may be determined that the cardiac conduction system pacing therapy has selective capture 346. Conversely, if less than or equal to 5 change events occur within the derivative signal over the sensing period, then it may be determined that the cardiac conduction system pacing therapy has non-selective capture 348. Although the change event threshold in this example is 5, the change event threshold may be less than 5 or greater than 5. For example, the change event threshold may be between about 2 and about 10, depending on the length of the sensing time period, among other things.

A change event may generally be described as an event where the derivative signal changes sign from positive-to-negative or positive-to-negative. For example, a minimum change threshold may be used such as, e.g., 0.1 Volts. Thus, a change event may be counted or determined for every sign change that is greater than 0.1 Volt within the derivative signal over the sensing period. Although the minimum change threshold in this example is 0.1 Volts, the minimum change threshold may be less than 0.1 Volts or greater than 0.1 Volts. For example, the minimum change threshold may be between about 0.05 Volts and about 0.4 Volts.

Figure 12A:
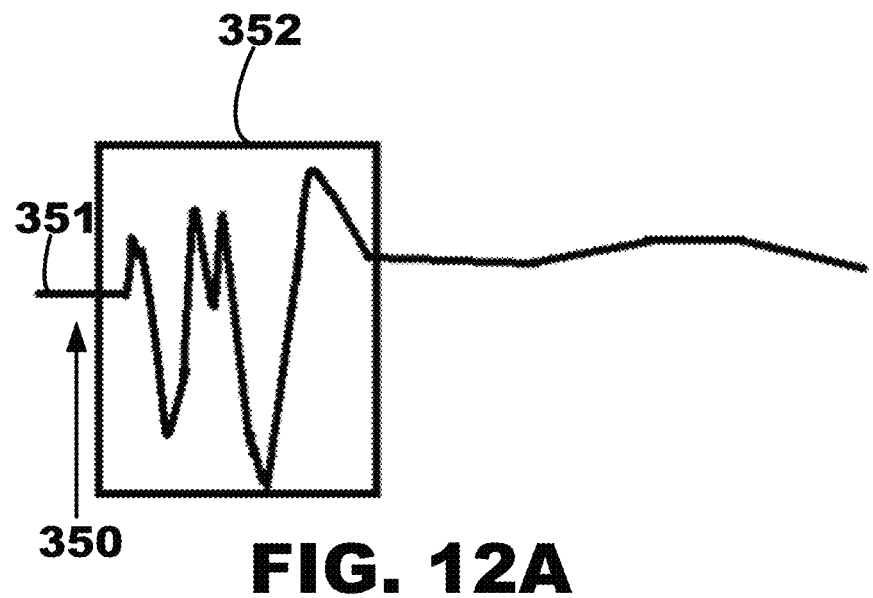
FIG. 12A depicts a left bunch branch electrocardiogram showing selective cardiac conduction system capture.
Figure 12B:
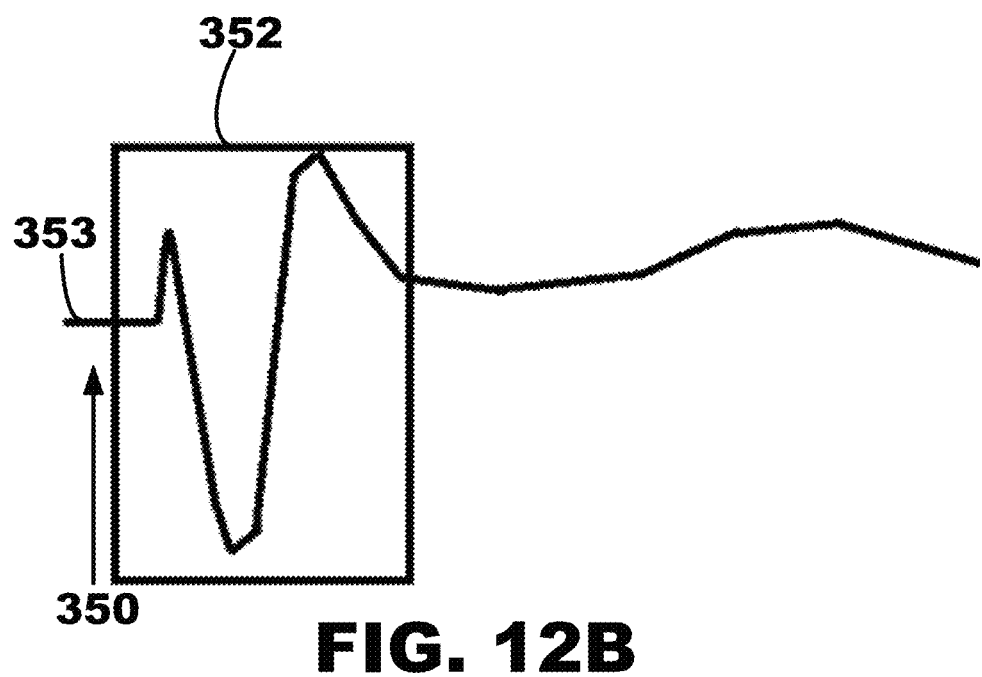
FIG. 12B depicts a left bunch branch electrocardiogram showing non-selective cardiac conduction system capture.

A left bunch branch electrocardiogram 351 showing selective cardiac conduction system capture is depicted in FIG. 12A. As shown, more than 5 change events have occurred within the sensing time period 352 following the cardiac conduction system pacing therapy 350 thereby indicating selective capture of the cardiac conduction system. A left bunch branch electrocardiogram 353 showing non-selective cardiac conduction system capture is depicted in FIG. 12B. As shown, less than or equal to 5 change events have occurred within the sensing time period 352 following the cardiac conduction system pacing therapy 350 thereby indicating non-selective capture of the cardiac conduction system.

Various examples have been described. These and other examples are within the scope of the following claims. For example, a single chamber, dual chamber, or triple chamber pacemakers (e.g., CRT-P) or ICDs (e.g., CRT-D) devices can be used to implement the illustrative methods described herein.

ILLUSTRATIVE EXAMPLES

While the present disclosure is not so limited, an appreciation of various aspects of the disclosure will be gained through a discussion of the specific illustrative examples provided below. Various modifications of the illustrative examples, as well as additional examples of the disclosure, will become apparent herein.

Example 1: An implantable medical device comprising:
a plurality of implantable electrodes to sense and pace a patient's heart, wherein the plurality of electrodes comprise:
 a left ventricular electrode positionable proximate the patient's left ventricle; and
 a cardiac conduction system electrode positionable proximate a portion of the patient's cardiac conduction system; and
a computing apparatus comprising processing circuitry, the computing apparatus operably coupled to the plurality of implantable electrodes, wherein the computing apparatus is configured to:
 initiate delivery of cardiac conduction system pacing therapy to the patient's cardiac conduction system using the cardiac conduction system electrode;
 monitor local electrical activity of the patient using the left ventricular electrode during the delivery of cardiac conduction system pacing therapy using the cardiac conduction system electrode; and
 switch to delivery of both cardiac conduction system pacing therapy to the patient's cardiac conduction system using the cardiac conduction system electrode and left ventricular pacing therapy to the patient's left ventricle using the left ventricular electrode in response to the monitored local electrical activity.

Example 2: A method comprising:
 delivering cardiac conduction system pacing therapy to a patient's cardiac conduction system using a cardiac conduction system electrode implanted proximate a portion of the patient's cardiac conduction system;
 monitoring local electrical activity of the patient using a left ventricular electrode implanted proximate the patient's left ventricle during the delivery of cardiac conduction system pacing therapy using the cardiac conduction system electrode; and
 switching to delivery of both cardiac conduction system pacing therapy to the patient's cardiac conduction system using the cardiac conduction system electrode and left ventricular pacing therapy to the patient's left ventricle using the left ventricular electrode in response to the monitored local electrical activity.

Example 3: The device of Example 1 or the method of Example 2, wherein the cardiac conduction system electrode is positioned proximate the patient's bundle of His to deliver cardiac conduction system pacing therapy thereto.

Example 4: The device or method as in any one of Examples 1-3, wherein the cardiac conduction system electrode is positioned proximate the patient's left bundle branch bundle to deliver cardiac conduction system pacing therapy thereto.

Example 5: The device or method as in any one of Examples 1-3, the computing apparatus is further configured to execute or the method further comprising determining an interval between the delivery of the cardiac conduction system pacing therapy and a peak of the monitored local electrical activity, wherein switching to delivery of both cardiac conduction system pacing therapy to the patient's cardiac conduction system using the cardiac conduction system electrode and left ventricular pacing therapy to the patient's left ventricle using the left ventricular electrode in response to the monitored local electrical activity is based on the interval.

Example 6: The device or method of Example 5, the computing apparatus is further configured to execute or the method further comprising adjusting a cardiac conduction system pacing output parameter in response to the interval being greater than or equal to a threshold.

Example 7: The device or method of Example 6, wherein the threshold is less than or equal to 50 milliseconds.

Example 8: The device or method of Example 5, wherein switching to delivery of both cardiac conduction system pacing therapy and left ventricular pacing therapy in response to the monitored local electrical activity comprises switching to delivery of both cardiac conduction system pacing therapy and left ventricular pacing therapy in response to the interval being greater than or equal to the threshold.

Example 9: The device or method as in any one of Examples 1-8, the computing apparatus is further configured to execute or the method further comprising:
 periodically ceasing delivery of pacing therapy and monitor intrinsic electrical activity of the patient using the left ventricular electrode during intrinsic cardiac electrical activation; and
 determining a paced AV delay for use in delivery of cardiac conduction system pacing therapy using the cardiac conduction system electrode based on the monitored intrinsic electrical activity, wherein the paced AV delay is a time period between an atrial event and delivery of cardiac conduction system pacing therapy.

Example 10: An implantable medical device comprising:
a plurality of implantable electrodes to sense and pace a patient's heart, wherein the plurality of electrodes comprise:

a left ventricular electrode positionable proximate the patient's left ventricle; and a cardiac conduction system electrode positionable proximate a portion of the patient's cardiac conduction system; and a computing apparatus comprising processing circuitry, the computing apparatus operably coupled to the plurality of implantable electrodes, wherein the computing apparatus is configured to:

determine a paced AV delay for use in delivery of cardiac conduction system pacing therapy using the cardiac conduction system electrode, wherein the paced AV delay is a time period between an atrial event and delivery of cardiac conduction system pacing therapy;

determine a paced VV delay for use in delivery of cardiac conduction system pacing therapy using the cardiac conduction system electrode and delivery of left ventricular pacing therapy using the left ventricular electrode, wherein the paced VV delay is a time period between the delivery of the left ventricular pacing therapy and the delivery of the cardiac conduction system pacing therapy; and deliver either cardiac conduction system pacing therapy using the paced AV delay or cardiac conduction system pacing therapy and left ventricular pacing therapy using the paced AV delay and the paced VV delay.

Example 11: A method comprising determining a paced AV delay for use in delivery of cardiac conduction system pacing therapy using a cardiac conduction system electrode implanted proximate a portion of the patient's cardiac conduction system, wherein the paced AV delay is a time period between an atrial event and delivery of cardiac conduction system pacing therapy;

determining a paced VV delay for use in delivery of cardiac conduction system pacing therapy using the cardiac conduction system electrode and delivery of left ventricular pacing therapy using a left ventricular electrode implanted proximate the patient's left ventricle, wherein the paced VV delay is a time period between the delivery of the left ventricular pacing therapy and the delivery of the cardiac conduction system pacing therapy; and delivering either cardiac conduction system pacing therapy using the paced AV delay or cardiac conduction system pacing therapy and left ventricular pacing therapy using the paced AV delay and the paced VV delay.

Example 12: The device of Example 10 or the method of Example 11, wherein the cardiac conduction system electrode is positioned proximate the patient's bundle of His to deliver cardiac conduction system pacing therapy thereto.

Example 13: The device of Example 10 or the method of Example 11, wherein the cardiac conduction system electrode is positioned proximate the patient's left bundle branch bundle to deliver cardiac conduction system pacing therapy thereto.

Example 14: The device or method as in any one of Examples 10-13, wherein determining the paced AV delay comprises:

initiating delivery of cardiac conduction system pacing therapy to the patient's cardiac conduction system using the cardiac conduction system electrode at a plurality of different paced AV delays;

monitoring far-field electrical activity of the patient during the delivery of cardiac conduction system pacing therapy; and selecting a paced AV delay of the plurality of different paced AV delays based on the far-field electrical activity monitored during the delivery of cardiac conduction system pacing therapy.

Example 15: The device or method of Example 14, wherein selecting the paced AV delay of the plurality of different paced AV delays based on the far-field electrical activity monitored during the delivery of cardiac conduction system pacing therapy comprises selecting the paced AV delay of the plurality of different paced AV delays providing a shortest time period between the delivery of the cardiac conduction system pacing therapy and an end of ventricular depolarization.

Example 16: The device or method as in any one of Examples 14-15, wherein determining the paced AV delay further comprises monitoring far-field electrical activity of the patient prior to delivery of pacing therapy to provide an intrinsic AV delay between an intrinsic atrial event and an intrinsic ventricular event, wherein the plurality of different paced AV delays are less than the intrinsic AV delay.

Example 17: The device or method as in any one of Examples 14-16, wherein the far-field electrical activity is monitored using the left ventricular electrode.

Example 18: The device or method as in any one of Examples 14-16, wherein the far-field electrical activity is monitored using at least one external electrode attached to the patient's skin.

Example 19: The device or method as in any one of Examples 10-19, wherein determining the paced VV delay comprises initiating delivery of left ventricular pacing therapy to the patient's left ventricle using the left ventricular electrode and cardiac conduction system pacing therapy to the patient's cardiac conduction system using the cardiac conduction system electrode at the paced AV delay and at a plurality of different paced VV delays, monitoring far-field electrical activity of the patient during the delivery of left ventricular pacing therapy and cardiac conduction system pacing therapy; and selecting a paced VV delay of the plurality of different paced AV delays based on the electrical activity monitored during the delivery of left ventricular pacing therapy and cardiac conduction system pacing therapy.

Example 20: The device of method of Example 19, wherein selecting the paced VV delay of the plurality of different paced VV delays based on the far-field electrical activity monitored during the delivery of left ventricular and cardiac conduction system pacing therapy comprises selecting the paced VV delay of the plurality of different paced VV delays providing a shortest time period between the delivery of the left ventricular and cardiac conduction system pacing therapy and an end of ventricular depolarization.

Example 21: An implantable medical device comprising:

a plurality of implantable electrodes to sense and pace a patient's heart; and a computing apparatus comprising processing circuitry, the computing apparatus operably coupled to the plurality of implantable electrodes and configured to:

initiate a delivery of pacing therapy to the patient's heart;

monitor a near-field signal over a sensing time period proximate the left bundle branch using the plurality of implantable electrodes following the delivery of pacing therapy;

generate a derivative signal based on the near-field signal; and determine whether the pacing therapy has selective or non-selective capture of the cardiac conduction system based on the derivative signal.

Example 22: A method comprising:

delivering pacing therapy to the patient's heart using one or more of a plurality of implantable electrodes;

monitoring a near-field signal over a sensing time period proximate the left bundle branch using the plurality of implantable electrodes following the delivery of pacing therapy;

generating a derivative signal based on the near-field signal; and determining whether the pacing therapy has selective or non-selective capture of the cardiac conduction system based on the derivative signal.

Example 23: The method of Example 22, wherein generating the derivative signal based on the near-field signal comprises generating a 5-point derivative of the near-field signal.

Example 24: The device of Example 22 or the method of Example 23, wherein determining whether the pacing therapy has selective or non-selective capture of the cardiac conduction system based on the derivative signal comprises determining a number of change events within the derivative signal over the sensing time period.

Example 25: The device or method of Example 24, wherein a change event is a 0.1 Volt change.

Example 26: The device or method as in any one of Examples 24-25, wherein determining whether the pacing therapy has selective or non-selective capture of the cardiac conduction system based on the derivative signal further comprises determining that the pacing therapy has selective capture of the cardiac conduction system if there are more than 5 change events during the sensing time period.

Example 27: The device or method as in any one of Examples 22-26, the computing apparatus is further configured to execute or the method further comprising adjusting one or more paced settings of the pacing therapy in response to determining that the pacing therapy has non-selective capture of the cardiac conduction system.

Example 28: The device or method as in any one of Examples 22-27, wherein the sensing time period is less than or equal to 50 milliseconds.

Example 29: The device or method as in any one of Examples 22-28, wherein the near-field signal is sensed following a blanking time period after the delivery of pacing therapy Example 30: The device or method of Example 29, wherein the blanking time period is less than or equal to 20 milliseconds.

This disclosure has been provided with reference to illustrative embodiments and examples and is not meant to be construed in a limiting sense. As described previously, one skilled in the art will recognize that other various illustrative applications may use the techniques as described herein to take advantage of the beneficial characteristics of the devices and methods described herein. Various modifications of the illustrative embodiments and examples will be apparent upon reference to this description.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a mobile user device may be operatively coupled to a cellular network transmit data to or receive data therefrom).

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed:

1. An implantable medical device comprising:
   a plurality of implantable electrodes to sense and pace a patient's heart, wherein the plurality of electrodes comprise:
      a left ventricular electrode positionable proximate the patient's left ventricle; and
      a cardiac conduction system electrode positionable proximate a portion of the patient's cardiac conduction system; and
   a computing apparatus comprising processing circuitry, the computing apparatus operably coupled to the plurality of implantable electrodes, wherein the computing apparatus is configured to:
      initiate delivery of cardiac conduction system pacing therapy to the patient's cardiac conduction system using the cardiac conduction system electrode;
      monitor local electrical activity of the patient using the left ventricular electrode during the delivery of cardiac conduction system pacing therapy using the cardiac conduction system electrode; and
      switch to delivery of both cardiac conduction system pacing therapy to the patient's cardiac conduction system using the cardiac conduction system electrode and left ventricular pacing therapy to the patient's left ventricle using the left ventricular electrode in response to the monitored local electrical activity.

2. The device of claim 1, wherein the cardiac conduction system electrode is positionable proximate the patient's bundle of His to deliver cardiac conduction system pacing therapy thereto.

3. The device of claim 1, wherein the cardiac conduction system electrode is positionable proximate the patient's left bundle branch bundle to deliver cardiac conduction system pacing therapy thereto.

4. The device of claim 1, wherein the computing apparatus is further configured to determine an interval between the delivery of the cardiac conduction system pacing therapy and a peak of the monitored local electrical activity, wherein switching to delivery of both cardiac conduction system pacing therapy to the patient's cardiac conduction system using the cardiac conduction system electrode and left ventricular pacing therapy to the patient's left ventricle using the left ventricular electrode is based on the interval.

5. The device of claim 4, wherein the computing apparatus is further configured to adjust a cardiac conduction system pacing output parameter in response to the interval being greater than or equal to a threshold.

6. The device of claim 5, wherein the threshold is less than or equal to 50 milliseconds.

7. The device of claim 4, wherein switching to delivery of both cardiac conduction system pacing therapy and left ventricular pacing therapy in response to the monitored local electrical activity comprises switching to delivery of both cardiac conduction system pacing therapy and left ventricular pacing therapy in response to the interval being greater than or equal to the threshold.

8. The device of claim 1, wherein the computing apparatus is further configured to:
   periodically cease delivery of pacing therapy and monitor intrinsic electrical activity of the patient using the left ventricular electrode during intrinsic cardiac electrical activation; and
   determine a paced AV delay for use in delivery of cardiac conduction system pacing therapy using the cardiac conduction system electrode based on the monitored intrinsic electrical activity, wherein the paced AV delay is a time period between an atrial event and delivery of cardiac conduction system pacing therapy.

9. A method comprising:
   delivering cardiac conduction system pacing therapy to a patient's cardiac conduction system using a cardiac conduction system electrode implanted proximate a portion of the patient's cardiac conduction system;
   monitoring local electrical activity of the patient using a left ventricular electrode implanted proximate the patient's left ventricle during the delivery of cardiac conduction system pacing therapy using the cardiac conduction system electrode; and
   switching to delivery of both cardiac conduction system pacing therapy to the patient's cardiac conduction system using the cardiac conduction system electrode and left ventricular pacing therapy to the patient's left ventricle using the left ventricular electrode in response to the monitored local electrical activity.

10. The method of claim 9, wherein the cardiac conduction system electrode is positioned proximate the patient's bundle of His to deliver cardiac conduction system pacing therapy thereto.

11. The method of claim 9, wherein the cardiac conduction system electrode is positioned proximate the patient's left bundle branch bundle to deliver cardiac conduction system pacing therapy thereto.

12. The method of claim 9, the method further comprising determining an interval between the delivery of the cardiac conduction system pacing therapy and a peak of the monitored local electrical activity, wherein switching to delivery of both cardiac conduction system pacing therapy to the patient's cardiac conduction system using the cardiac conduction system electrode and left ventricular pacing therapy to the patient's left ventricle using the left ventricular electrode in response to the monitored local electrical activity is based on the interval.

13. The method of claim 12, the method further comprising adjusting a cardiac conduction system pacing output parameter in response to the interval being greater than or equal to a threshold.

14. The method of claim 13, wherein the threshold is less than or equal to 50 milliseconds.

15. The method of claim 12, wherein switching to delivery of both cardiac conduction system pacing therapy and left ventricular pacing therapy in response to the monitored local electrical activity comprises switching to delivery of both cardiac conduction system pacing therapy and left ventricular pacing therapy in response to the interval being greater than or equal to the threshold.

16. The method of claim 9, the method further comprising:

periodically ceasing delivery of pacing therapy and monitor intrinsic electrical activity of the patient using the left ventricular electrode during intrinsic cardiac electrical activation; and determining a paced AV delay for use in delivery of cardiac conduction system pacing therapy using the cardiac conduction system electrode based on the monitored intrinsic electrical activity, wherein the paced AV delay is a time period between an atrial event and delivery of cardiac conduction system pacing therapy.

* * * * *